United States Patent
Sano

(10) Patent No.: US 8,905,940 B2
(45) Date of Patent: Dec. 9, 2014

(54) FLOW RATE CONTROL VALVE AND BLOOD PRESSURE INFORMATION MEASUREMENT DEVICE INCLUDING THE SAME

(75) Inventor: Yoshihiko Sano, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 14/000,738

(22) PCT Filed: Apr. 5, 2012

(86) PCT No.: PCT/JP2012/059325
§ 371 (c)(1),
(2), (4) Date: Aug. 21, 2013

(87) PCT Pub. No.: WO2012/141064
PCT Pub. Date: Oct. 18, 2012

(65) Prior Publication Data
US 2013/0331715 A1 Dec. 12, 2013

(30) Foreign Application Priority Data

Apr. 11, 2011 (JP) ................................. 2011-087458

(51) Int. Cl.
| | | |
|---|---|---|
| *A61B 5/02* | (2006.01) | |
| *A61B 5/0235* | (2006.01) | |
| *F16K 7/17* | (2006.01) | |
| *F16K 31/00* | (2006.01) | |
| *G05D 7/00* | (2006.01) | |

(52) U.S. Cl.
CPC ............... *A61B 5/0235* (2013.01); *F16K 7/17* (2013.01); *F16K 31/004* (2013.01); *G05D 7/005* (2013.01)
USPC ............................................................ 600/498

(58) Field of Classification Search
USPC .................................................. 600/485–515
See application file for complete search history.

(56) References Cited

U.S. PATENT DOCUMENTS 4,178,918 A * 12/1979 Cornwell ...................... 600/495
4,587,974 A * 5/1986 Link .............................. 600/498
(Continued)

FOREIGN PATENT DOCUMENTS

| JP | A-06-047007 | 2/1994 |
| JP | A-06-047008 | 2/1994 |

(Continued)

OTHER PUBLICATIONS

Jul. 17, 2012 International Search Report issued in International Patent Application No. PCT/JP2012/059325.

(Continued)

*Primary Examiner* — Michael Kahelin
*Assistant Examiner* — Mitchell E Alter
(74) *Attorney, Agent, or Firm* — Oliff PLC

(57) ABSTRACT

A flow rate control valve includes a casing provided with an inlet port and an outlet port through which a fluid, the flow rate of which should be controlled, flows in and out, a diaphragm that partitions a space inside the casing into a flow space in which the fluid flows and a working space in which a working medium is present, and a valve body provided on a portion of the diaphragm that opposes the inlet port. The diaphragm is displaced in accordance with a change in the internal pressure of the working space, and the valve body is accordingly moved. This results in a change in the distance between the valve body and the inlet port, and thus the flow rate of the fluid flowing into the flow space through the inlet port is adjusted. Therefore, the flow rate of the fluid flowing out through the outlet port is variably controlled.

17 Claims, 25 Drawing Sheets

(56) References Cited

U.S. PATENT DOCUMENTS

| | | | |
|---|---|---|---|
| 6,164,933 A * | 12/2000 | Tani et al. | 417/413.2 |
| 2003/0111178 A1 | 6/2003 | Morita | |
| 2003/0120157 A1 | 6/2003 | Fukui et al. | |
| 2005/0217267 A1 | 10/2005 | Tsuzuki et al. | |
| 2007/0060826 A1 * | 3/2007 | Krauter | 600/498 |
| 2008/0099081 A1 | 5/2008 | Yamamoto | |

FOREIGN PATENT DOCUMENTS

| | | |
|---|---|---|
| JP | A-2002-005330 | 1/2002 |
| JP | A-2002-089725 | 3/2002 |
| JP | A-2003-185053 | 7/2003 |
| JP | A-2005-291150 | 10/2005 |
| JP | A-2006-070946 | 3/2006 |
| JP | A-2007-239769 | 9/2007 |
| JP | A-2011-057179 * | 9/2009 |
| JP | A-2009-250132 | 10/2009 |
| JP | A-2010-225788 | 10/2010 |
| JP | A-2011-057179 | 3/2011 |
| WO | WO 2010/103885 A1 | 9/2010 |
| WO | WO 2010/137578 A1 | 12/2010 |

OTHER PUBLICATIONS

Feb. 15, 2013 International Preliminary Report on Patentability issued in International Patent Application No. PCT/JP2012/059325 (with translation).

* cited by examiner

FLOW RATE CONTROL VALVE AND BLOOD PRESSURE INFORMATION MEASUREMENT DEVICE INCLUDING THE SAME

TECHNICAL FIELD

The present invention relates to a flow rate control valve that can variably control the flow rate of a fluid and a blood pressure information measurement device including the flow rate control valve, and more particularly relates to a flow rate control valve that can variably control the flow rate of a compressed fluid and a blood pressure information measurement device including the flow rate control valve as a discharge valve for reducing the internal pressure of a compressing fluid bladder.

BACKGROUND ART

Measuring blood pressure information of a subject is extremely important in gaining an understanding of the state of health of the subject. In recent years, attempts have been made to determine the cardiac stress or the level of arteriosclerosis not only by measuring a systolic blood pressure value and a diastolic blood pressure value, the usefulness of which as typical indices that contribute to analysis of the risk of cardiovascular diseases such as stroke, heart failure, myocardial infarction, and the like has been widely acknowledged, but also, for example, by measuring the pulse wave of the subject.

Blood pressure information measurement devices are devices for measuring blood pressure information, and are expected to be further used in fields such as early detection, prevention, and treatment of circulatory diseases. It should be noted that the blood pressure information includes a wide variety of types of circulatory information, such as systolic blood pressure values, diastolic blood pressure values, average blood pressure values, the pulse wave, the pulse, various indices indicating the level of arteriosclerosis, and the like.

Generally, a cuff for a blood pressure information measurement device (hereinafter also simply referred to as "cuff") is used to measure blood pressure information. Here, "cuff" means a band- or ring-shaped structure that contains a fluid bladder with an inner cavity and that can be attached to a part of a living body, and refers to those for use in measurement of blood pressure information, where an artery is compressed by inflating the fluid bladder by injecting a fluid, such as a gas, a liquid, or the like, into the aforementioned inner cavity.

Usually, a blood pressure information measurement device is provided with a pressurization pump and a discharge valve, which serve as a pressurization/depressurization mechanism for increasing/reducing the internal pressure of the fluid bladder. Of these two components, the discharge valve is intended to maintain the internal pressure of the fluid bladder in a closed state in which the discharge valve is closed, the internal pressure having been increased by the pressurization pump, and to reduce the internal pressure in an opened state in which the discharge valve is opened. A flow rate control valve, the operation of which is controlled when reducing the internal pressure of the fluid bladder and which thus can variably control the discharge flow rate, is preferably used as the discharge valve.

Conventionally, as disclosed in, for example, JP 6-47007A (Patent Literature 1), JP 6-47008A (Patent Literature 2), JP 2002-5330A (Patent Literature 3), and the like, solenoid valves whose valve bodies are electromagnetically driven have been commonly used as the flow rate control valve serving as the discharge valve.

Here, a solenoid valve includes a housing, a drive shaft with a valve body attached to an end, a permanent magnet provided in either the housing or the drive shaft, and an electromagnetic coil provided in the other of the housing and the drive shaft, and is configured so that the drive shaft can be moved in an axial direction by means of an electromagnetic force, which is generated in the electromagnetic coil by supplying current to the electromagnetic coil, and a repulsive force, which is then generated in the permanent magnet.

In each of the blood pressure information measurement devices disclosed in JP 6-47007A, JP 6-47008A, and JP 2002-5330A above, the solenoid valve is disposed opposite to a discharge port of the fluid bladder contained in the cuff, the valve body attached to the end of the drive shaft is configured so as to be able to close and open the discharge port as it moves, and thus the flow rate of the fluid discharged from the fluid bladder can be variably controlled.

CITATION LIST

Patent Literature

Patent Literature 1: JP 6-47007A
Patent Literature 2: JP 6-47008A
Patent Literature 3: JP 2002-5330A

SUMMARY OF INVENTION

Technical Problem

However, when a flow rate control valve composed of a solenoid valve is employed as a discharge valve provided in a blood pressure information measurement device, the following problems arise.

First, as described above, solenoid valves have a configuration in which the drive shaft is moved by means of the electromagnetic force that is generated in the electromagnetic coil and the repulsive force that is generated in the permanent magnet, and thus consume more electricity than other actuators. Therefore, when a solenoid valve is used as the discharge valve, a problem arises in that the power consumption of the entire blood pressure information measurement device is also increased.

Second, as described above, solenoid valves contain various components such as the permanent magnet, the electromagnetic coil, and the like, and thus are relatively expensive, have extremely complicated structures, and are also large in volume. Therefore, when a solenoid valve is used as the discharge valve, problems arise in that the manufacturing cost of the blood pressure information measurement device is affected and that the size and the weight of the blood pressure information measurement device are increased.

Third, as described above, solenoid valves have a configuration in which the drive shaft is moved by means of the electromagnetic force that is generated in the electromagnetic coil and the repulsive force that is generated in the permanent magnet, and it is thus relatively difficult to precisely control the travel distance of the drive shaft. Therefore, when a solenoid valve is used as the discharge valve, a problem arises in that it becomes difficult to precisely control the flow rate of the fluid discharged from the fluid bladder.

In this manner, conventional blood pressure information measurement devices and flow rate control valves serving as discharge valves provided in those blood pressure information measurement devices still have much room for improvement in various respects as described above.

Therefore, it is an object of the present invention to provide a flow rate control valve that can be configured to be compact, lightweight, and inexpensive, that achieves low power consumption, and that can easily control the flow rate of a fluid, and a blood pressure information measurement device including the flow rate control valve as a discharge valve.

Solution to Problem

A flow rate control valve according to the present invention is a flow rate control valve that can variably control a flow rate of a fluid, and includes a casing, a diaphragm, and a valve body. The casing is provided with an inlet port through which the fluid flows in and an outlet port through which the fluid flows out. The diaphragm partitions a space within the casing into a flow space in which the fluid flows and a working space in which a working medium is present. The valve body is provided on a portion of the diaphragm that opposes the inlet port. In the flow rate control valve according to the present invention, the diaphragm is displaced in accordance with a change in an internal pressure of the working space, the valve body is accordingly moved, resulting in a change in a distance between the valve body and the inlet port, and thus the flow rate of the fluid flowing into the flow space through the inlet port is adjusted, so that the flow rate of the fluid flowing out through the outlet port can be variably controlled.

In the flow rate control valve according to the present invention, it is preferable that a portion of the diaphragm that is displaced in accordance with a change in the internal pressure of the working space has a larger area than an opening area of the inlet port.

In the flow rate control valve according to the present invention, it is preferable that the valve body has a size that is sufficient to completely close the inlet port in a state in which the distance between the valve body and the inlet port is reduced to zero.

In the flow rate control valve according to the present invention, it is preferable that the valve body is composed of an elastic member.

In the flow rate control valve according to the present invention, it is preferable that the valve body is composed of a member that is harder than the diaphragm.

In the flow rate control valve according to the present invention, it is preferable that a principal surface of the valve body that opposes the inlet port has minute protrusions and recesses.

In the flow rate control valve according to the present invention, it is preferable that the casing is provided with an opening for introducing and releasing the working medium.

Preferably, the flow rate control valve according to the present invention further includes a pressure generating unit that produces a change in the internal pressure of the working space by introducing and releasing the working medium via the opening.

In the flow rate control valve according to the present invention, it is preferable that the pressure generating unit includes a pump that suctions and ejects the working medium.

In the flow rate control valve according to the present invention, it is preferable that assuming that a direction from the side of a suction port to the side of an ejection port of the pump is a forward direction, the pump is composed of a pump that can discharge the working medium in a reverse direction to the forward direction under a condition that a pressure on the side of the suction port is lower than a pressure on the side of the ejection port.

In the flow rate control valve according to the present invention, it is preferable that the pump is composed of a piezoelectric pump that suctions and ejects the working medium by vibration of a vibrating plate portion to which an piezoelectric element is attached.

In the flow rate control valve according to the present invention, assuming that a direction from the side of a suction port to the side of an ejection port of the pump is a forward direction, the pump may be composed of a pump that cannot discharge the working medium in a reverse direction to the forward direction under a condition that a pressure on the side of the suction port is lower than a pressure on the side of the ejection port, and in that case, it is preferable that an escape valve is provided so as to communicate with the working space.

In the flow rate control valve according to the present invention, it is preferable that the casing and the pressure generating unit are integrated by fixing the casing to a housing of the pressure generating unit.

In the flow rate control valve according to the present invention, the fluid flowing into the flow space through the inlet port may be compressed air that is compressed to a pressure greater than atmospheric pressure, and in that case, it is preferable that the working medium that is present in the working space is air at a pressure lower than the compressed air.

A blood pressure information measurement device according to the present invention includes the flow rate control valve according to the present invention as a discharge valve for reducing an internal pressure of a compressing fluid bladder for compressing a living body.

In the blood pressure information measurement device according to the present invention, it is preferable that during measurement, driving of the flow rate control valve serving as the discharge valve is controlled so that the internal pressure of the compressing fluid bladder is slowly reduced, and thus at least a systolic blood pressure value and a diastolic blood pressure value are calculated based on a depressurization measurement method. Moreover, it is preferable that after completion of measurement, driving of the flow rate control valve serving as the discharge valve is controlled so that the internal pressure of the compressing fluid bladder is quickly reduced.

In the blood pressure information measurement device according to the present invention, it is preferable that during measurement, driving of the flow rate control valve serving as the discharge valve is controlled so that the internal pressure of the compressing fluid bladder is slowly increased, and thus at least a systolic blood pressure value and a diastolic blood pressure value are calculated based on a pressurization measurement method. Moreover, it is preferable that after completion of measurement, driving of the flow rate control valve serving as the discharge valve is controlled so that the internal pressure of the compressing fluid bladder is quickly reduced.

Advantageous Effects of Invention

According to the present invention, it is possible to provide a flow rate control valve that can be configured to be compact, lightweight, and inexpensive, that achieves low power consumption, and that can easily control the flow rate of a fluid, and a blood pressure information measurement device including the flow rate control valve as a discharge valve.

DESCRIPTION OF EMBODIMENTS

Figure 1:
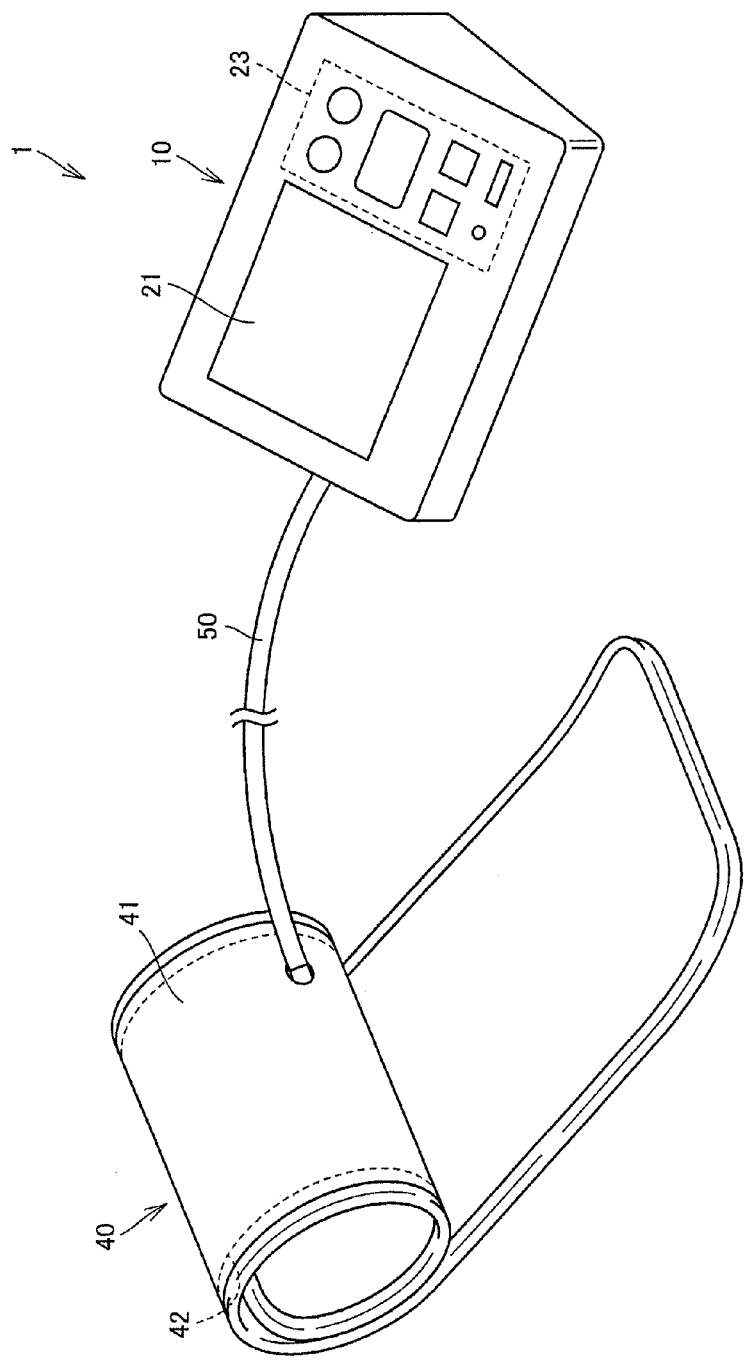
FIG. 1 is a perspective view showing an appearance of a sphygmomanometer of Embodiment 1 of the invention.

Hereinafter, embodiments of the present invention will be described in detail with reference to the drawings. In the following description of the embodiments, a so-called upper arm sphygmomanometer having a cuff that is used while applied to the upper arm of a subject and enabling measurement of a systolic blood pressure value and a diastolic blood pressure value of the subject will be used as an example of a blood pressure information measurement device. It should be noted that in the embodiments described below, parts that are the same or common will be denoted by the same reference signs in the drawings, and descriptions thereof will not be repeated.

Embodiment 1

Figure 2:
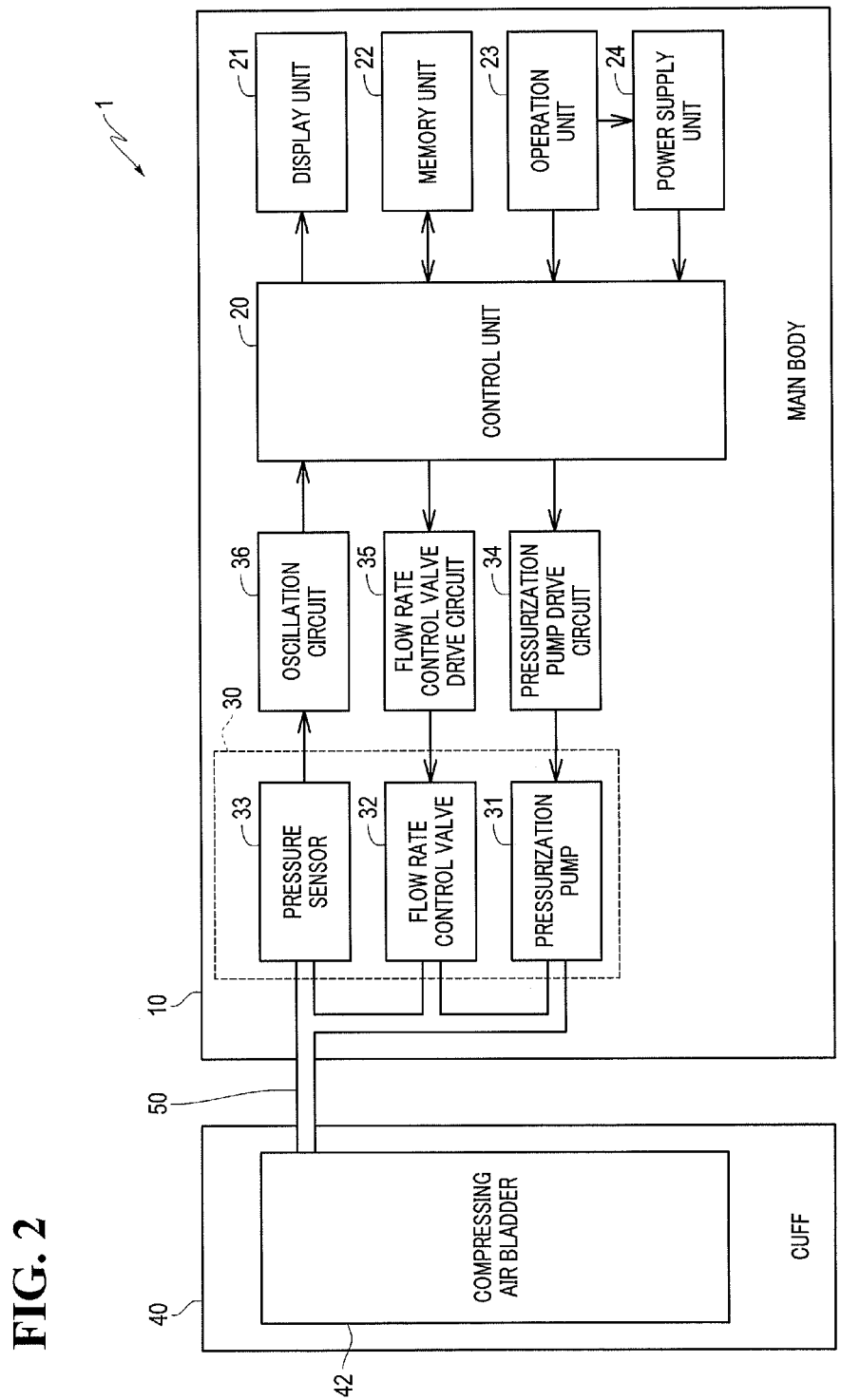
FIG. 2 is a diagram showing the configuration of functional blocks of the sphygmomanometer of Embodiment 1 of the invention.

FIG. 1 is a perspective view showing an appearance of a sphygmomanometer of Embodiment 1 of the invention, and FIG. 2 is a diagram showing the configuration of functional blocks. With reference to FIGS. 1 and 2, the configuration of a sphygmomanometer 1 of this embodiment will be described first.

As shown in FIG. 1, the sphygmomanometer 1 of this embodiment includes a main body 10, a cuff 40, and an air tube 50. The main body 10 has a box-shaped cabinet and has a display unit 21 and an operation unit 23 on an upper surface of the cabinet. During measurement, the main body 10 is used while mounted on a mounting surface such as a table. The cuff 40 mainly has a band- and bag-shaped outer package cover 41 and a compressing air bladder 42, which is a compressing fluid bladder, contained in the outer package cover 41, and has an approximately annular form as a whole. During measurement, the cuff 40 is used while wrapped around an upper arm of the subject. The air tube 50 connects the main body 10 and the cuff 40 to each other, which are configured separately.

As shown in FIG. 2, the main body 10 has, in addition to the aforementioned display unit 21 and operation unit 23, a control unit 20, a memory unit 22, a power supply unit 24, a pressurization pump 31, a flow rate control valve 32 serving as a discharge valve, a pressure sensor 33, a pressurization pump drive circuit 34, a flow rate control valve drive circuit 35, and an oscillation circuit 36. The pressurization pump 31, the flow rate control valve 32, and the pressure sensor 33 correspond to compressing air system components 30 that are provided in the sphygmomanometer 1, and in particular, the pressurization pump 31 and the flow rate control valve 32 correspond to a pressurization/depressurization mechanism for increasing/reducing the internal pressure of the compressing air bladder 42.

The compressing air bladder 42 is intended to compress the upper arm in a state in which it is placed thereon, and has an inner cavity inside. The compressing air bladder 42 is connected via the aforementioned air tube 50 to each of the aforementioned pressurization pump 31, flow rate control valve 32, and pressure sensor 33, which are the compressing air system components 30. Thus, the compressing air bladder 42 is pressurized and inflated by driving the pressurization pump 31, and the internal pressure of the compressing air bladder 42 is maintained or is reduced to deflate the compressing air bladder 42 by controlling driving of the flow rate control valve 32, which serves as a discharge valve.

The control unit 20 is configured by, for example, a CPU (Central Processing Unit) and is a means for performing overall control of the sphygmomanometer 1. The display unit 21 is configured by, for example, an LCD (Liquid Crystal Display) and is a means for displaying measurement results and the like. The memory unit 22 is configured by, for example, a ROM (Read-Only Memory) and a RAM (Random-Access Memory) and is a means for storing programs for causing the control unit 20 and the like to execute procedures for blood pressure measurement and storing measurement results and the like. The operation unit 23 is a means for accepting operations by the subject or the like and inputting the instructions from the outside to the control unit 20 and the power supply unit 24. The power supply unit 24 is a means for supplying electric power to the control unit 20.

The control unit 20 inputs control signals for driving the pressurization pump 31 and the flow rate control valve 32 to the pressurization pump drive circuit 34 and the flow rate control valve drive circuit 35, respectively, and inputs a blood pressure value, which is a measurement result, to the display unit 21 and the memory unit 22. Moreover, the control unit 20 includes a blood pressure information acquiring unit (not shown) that acquires a blood pressure value of the subject based on a pressure value detected by the pressure sensor 33. The blood pressure value acquired by this blood pressure information acquiring unit is then input to the aforementioned display unit 21 and memory unit 22 as a measurement result. It should be noted that the sphygmomanometer 1 may separately have an output unit that outputs a blood pressure value as a measurement result to an external device (e.g., a PC (Personal Computer), a printer, or the like). For example, a serial communication line, a writing device for writing to various types of recording media, and the like can be used as the output unit.

The pressurization pump drive circuit 34 controls the operation of the pressurization pump 31 based on the control signal input from the control unit 20. The flow rate control valve drive circuit 35 controls the opening and closing operation of the flow rate control valve 32 based on the control signal input from the control unit 20. The pressurization pump 31 is intended to increase the internal pressure (hereinafter also referred to as "cuff pressure") of the compressing air bladder 42 by supplying air into the inner cavity of the compressing air bladder 42, and the operation thereof is controlled by the aforementioned pressurization pump drive circuit 34. The flow rate control valve 32 is intended to maintain the internal pressure of the compressing air bladder 42 and to reduce the cuff pressure by opening the inner cavity of the compressing air bladder 42 to the outside, and the operation thereof is controlled by the aforementioned flow rate control valve drive circuit 35. The pressure sensor 33 detects the internal pressure of the compressing air bladder 42 and inputs an output signal corresponding to the detected internal pressure to the oscillation circuit 36. The oscillation circuit 36 generates a signal of an oscillation frequency corresponding to the signal input from the pressure sensor 33 and inputs the generated signal to the control unit 20.

In this embodiment, specifically, the flow rate control valve 32 is configured by a flow rate control valve 32A composed of a valve unit 100A and a piezoelectric pump unit 200A, which will be described later, and the flow rate control valve drive circuit 35 is configured by a piezoelectric element drive circuit 35A that controls driving of a piezoelectric element 260 provided in the piezoelectric pump unit 200A (see FIGS. 3 and 10 to 12, for example). The following is a detailed description of the flow rate control valve 32A of this embodiment.

Figure 3:
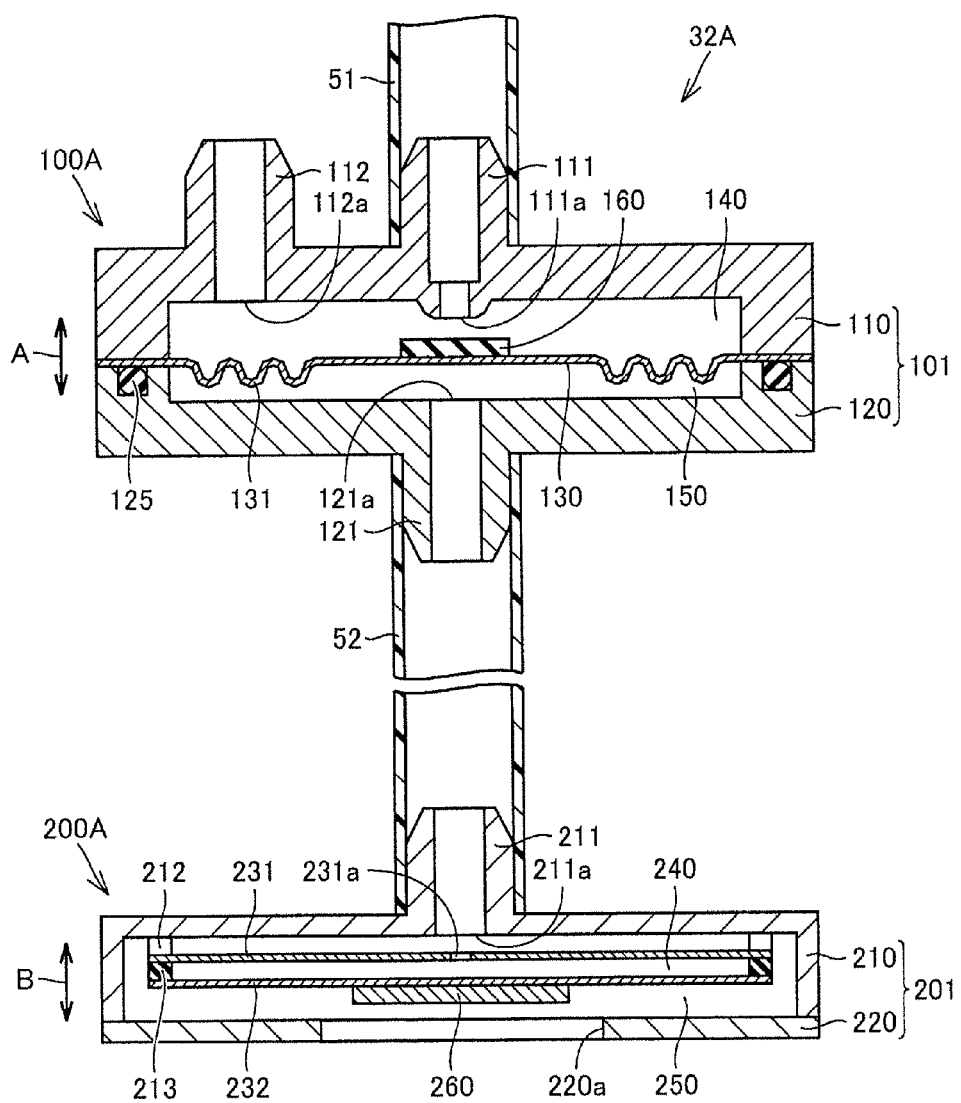
FIG. 3 is a schematic cross-sectional view of a flow rate control valve of Embodiment 1 of the invention.

FIG. 3 is a schematic cross-sectional view of the flow rate control valve of this embodiment. First, a specific configuration of the flow rate control valve 32A of this embodiment will be described.

As shown in FIG. 3, the flow rate control valve 32A of this embodiment is configured by combining the valve unit 100A and the piezoelectric pump unit 200A, which serves as a pressure generating unit. The valve unit 100A and the piezoelectric pump unit 200A are connected to each other via a connecting tube 52. Moreover, the flow rate control valve 32A is connected via a connecting tube 51 to the aforementioned compressing air bladder 42, pressurization pump 31, and pressure sensor 33.

The flow rate control valve 32A of this embodiment is configured so that compressed air, the flow rate of which is to be controlled, can flow from the compressing air bladder 42 into the valve unit 100A via the connecting tube 51, and so that air serving as a working medium can be introduced into the valve unit 100A from the piezoelectric pump unit 200A via the connecting tube 52 and can be released from the valve unit 100A to the piezoelectric pump unit 200A via the connecting tube 52. Therefore, in the flow rate control valve 32A, the pressure of the air serving as the working medium and being present in the valve unit 100A can be varied by controlling driving of the piezoelectric pump unit 200A, and thus the flow rate of the compressed air flowing into the valve unit 100A is adjusted, so that the flow rate of the compressed air flowing out of the valve unit 100A can be variably controlled.

As shown in FIG. 3, the valve unit 100A mainly includes a casing 101, a diaphragm 130, and a valve body 160. The casing 101 has a flat overall shape and is configured to have a space inside by combining a box-shaped upper case 110 whose lower end is open and a box-shaped lower case 120 whose upper end is open.

The diaphragm 130 is located between the upper case 110 and the lower case 120 and is fixed to the casing 101 by peripheral edges thereof being sandwiched by peripheral edges of each of the upper case 110 and the lower case 120. Thus, the diaphragm 130 is configured so as to be deflectable in the direction of arrow A in the drawing within the above-described space. It should be noted that a groove portion in which a seal member 125 composed of, for example, an O-ring or the like is accommodated is provided in the peripheral edges of the lower case 120, and the airtightness of the above-described space (especially the airtightness of a working space 150, which will be described later) is secured by that seal member 125 coming into contact with the diaphragm 130.

The space inside the casing 101 is partitioned by the diaphragm 130 into a space located on the side of the upper case 110 and a space located on the side of the lower case 120. The space located on the side of the upper case 110 is defined by the upper case 110 and the diaphragm 130 and corresponds to a flow space 140 in which the compressed air, the flow rate of which is to be controlled, flows. On the other hand, the space located on the side of the lower case 120 is defined by the lower case 120 and the diaphragm 130 and corresponds to the working space 150 in which air serving as the working medium is present.

An inlet portion 111, to which the connecting tube 51 is connected, is provided at a predetermined position of the upper case 110, and an inlet port 111a through which the compressed air flows in is provided in that inlet portion 111. Moreover, an outlet portion 112 is provided at a different position of the upper case 110, and an outlet port 112a through which the compressed air flows out is provided in that outlet portion 112. The inlet port 111a and the outlet port 112a each face the aforementioned flow space 140.

The valve body 160 is provided at a predetermined position of a principal surface on that side of the diaphragm 130 that faces the flow space 140. More specifically, the valve body 160 is disposed on a portion of the diaphragm 130 that opposes the inlet port 111a.

Here, in order to secure a larger amount of displacement of that portion of the diaphragm 130 on which the valve body 160 is provided, it is preferable that the valve body 160 is disposed on a central portion of the diaphragm 130, and therefore it is preferable that the aforementioned inlet port 111a is provided in a portion of the upper case 110 that faces the central portion of the diaphragm 130. Moreover, in order to increase the amount of displacement of the diaphragm 130 even more, it is preferable that a portion of the diaphragm 130 that faces the flow space 140 and the working space 150 has a circular shape.

A connecting portion 121, to which the connecting tube 52 is connected, is provided at a predetermined position of the lower case 120, and an opening 121a for introducing or releasing air serving as the working medium is provided in that connecting portion 121. The opening 121a faces the aforementioned working space 150.

The diaphragm 130 is made of a flexible member, and is composed of, for example, a thin film such as a metal film made of a stainless alloy, phosphor bronze, or the like, or a resin film made of a silicone resin, a polyester resin, a polyethylene terephthalate resin, or the like. On the other hand, the valve body 160 is preferably made of an elastic member, and is composed of, for example, a thick film member made of a silicone resin or the like. Here, the valve body 160 is preferably composed of a member that is harder than the diaphragm 130. It should be noted that in the case where the diaphragm 130 and the valve body 160 are formed of the same resin material, these components can also be composed of an integral member.

An easily deformable portion 131 formed by corrugating the diaphragm 130 is provided at a position of the diaphragm 130 that surrounds the portion on which the valve body 160 is provided. The easily deformable portion 131 is an area that is provided so as to make the diaphragm 130 more likely to be deflected, and when this area is provided, the amount of displacement of that portion of the diaphragm 130 on which the valve body 160 is provided can be increased even more.

Meanwhile, as shown in FIG. 3, the piezoelectric pump unit 200A mainly includes a housing 201, a thin plate portion 231, a vibrating plate portion 232, and the piezoelectric element 260. The housing 201 has a flat overall shape, and is configured to have a space inside by combining a box-shaped upper side housing 210 whose lower end is open and a flat plate-shaped lower side housing 220 that closes the lower end opening of the upper side housing 210.

A first support member 212 and a second support member 213 are provided inside the upper side housing 210. The first support member 212 fixes the aforementioned thin plate portion 231 at a predetermined distance from the upper side housing 210, and the second support member 213 fixes the aforementioned vibrating plate portion 232 at a predetermined distance from the thin plate portion 231. Thus, the vibrating plate portion 232 is configured so as to be deflectable in the direction of arrow B in the drawing within the above-described space.

The space inside the housing 201 is partitioned by the aforementioned thin plate portion 231, vibrating plate portion 232, and second support member 213 into a pumping space (pump compartment) 240 that is surrounded and hence defined by these members, and a surrounding space 250 that is defined by these members and the above-described housing 201 and located outside the above-described pumping space 240.

An ejection portion 211, to which the connecting tube 52 is connected, is provided at a predetermined position of the upper side housing 210, and an ejection port 211a through which air serving as the working medium is mainly ejected is provided in that ejection portion 211. The ejection port 211a faces the aforementioned surrounding space 250.

A minute communication hole 231a is provided at a predetermined position of the thin plate portion 231. More specifically, the minute communication hole 231a is disposed in a portion of the thin plate portion 231 that opposes the above-described ejection port 211a.

A suction port 220a through which air serving as the working medium is mainly suctioned is provided at a predetermined position of the lower side housing 220. The suction port 220a faces the aforementioned surrounding space 250.

The piezoelectric element 260 is provided at a predetermined position of a principal surface on that side of the vibrating plate portion 232 that faces the surrounding space 250. More specifically, the piezoelectric element 260 is disposed on a portion of the vibrating plate portion 232 that opposes the above-described suction port 220a. It should be noted that driving of the piezoelectric element 260 is controlled by the aforementioned piezoelectric element drive circuit 35A (see FIGS. 10 to 12).

Here, in order to secure a larger amount of displacement (i.e., amplitude) due to deflection of the vibrating plate portion 232, it is preferable that the piezoelectric element 260 is disposed on a central portion of the vibrating plate portion 232. Moreover, in order to increase the amount of displacement of the vibrating plate portion 232 even more, it is preferable that a portion of the vibrating plate portion 232 that faces the pumping space 240 and the surrounding space 250 has a circular shape. When the amount of displacement due to deflection of the vibrating plate portion 232 is increased by employing this configuration, the pumping power of the piezoelectric pump unit 200A can be enhanced even more.

Figure 4A:
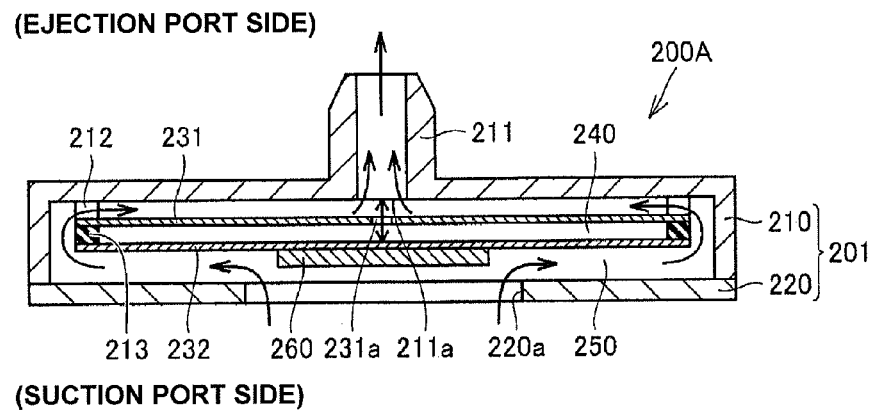
FIG. 4A is a schematic cross-sectional view showing an operating condition of a piezoelectric pump unit shown in FIG. 3.
Figure 4B:
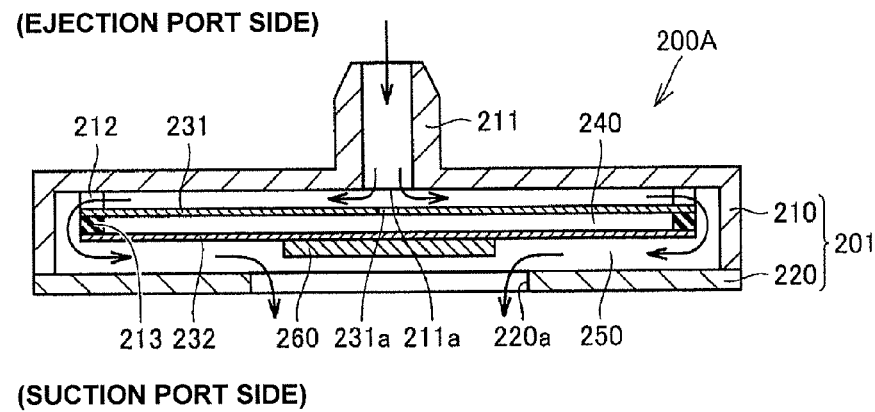
FIG. 4B is a schematic cross-sectional view showing an operating condition of the piezoelectric pump unit shown in FIG. 3.
Figure 5A:
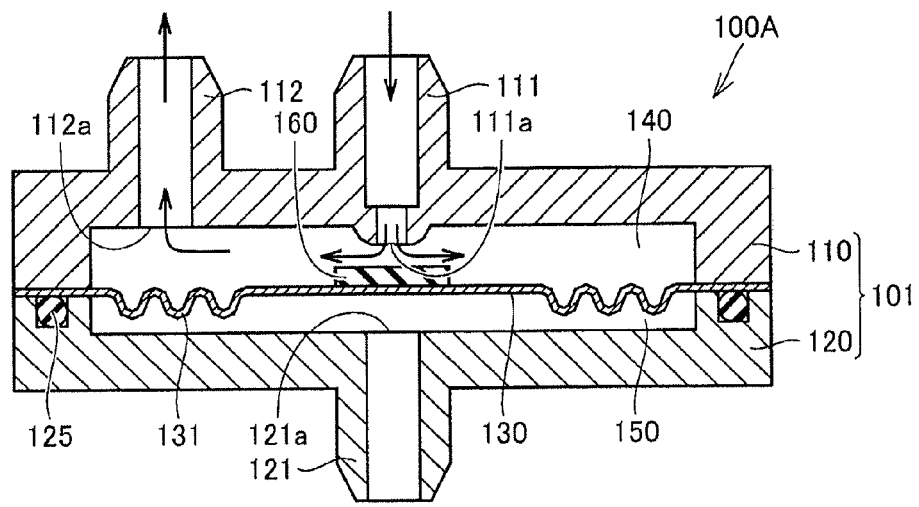
FIG. 5A is a schematic cross-sectional view showing an operating condition of a valve unit shown in FIG. 3.
Figure 5B:
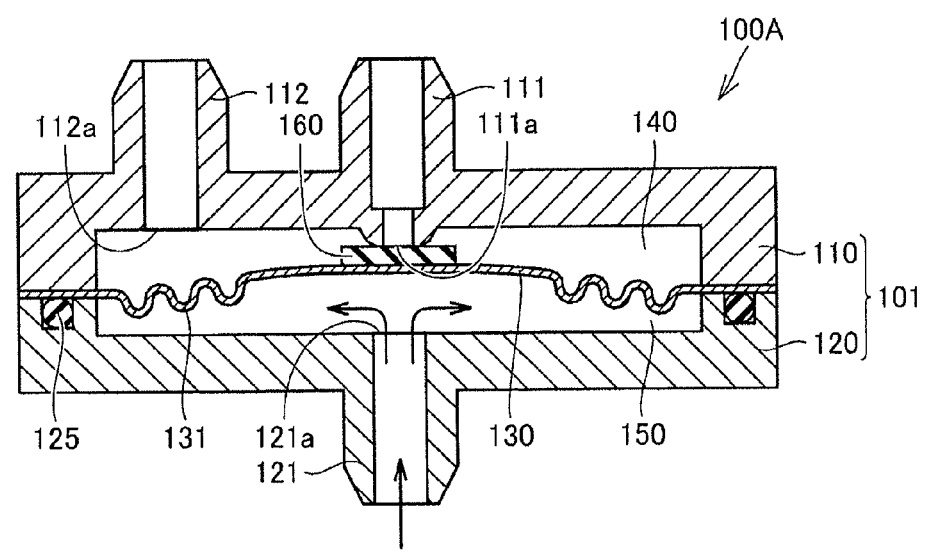
FIG. 5B is a schematic cross-sectional view showing an operating condition of the valve unit shown in FIG. 3.
Figure 5C:
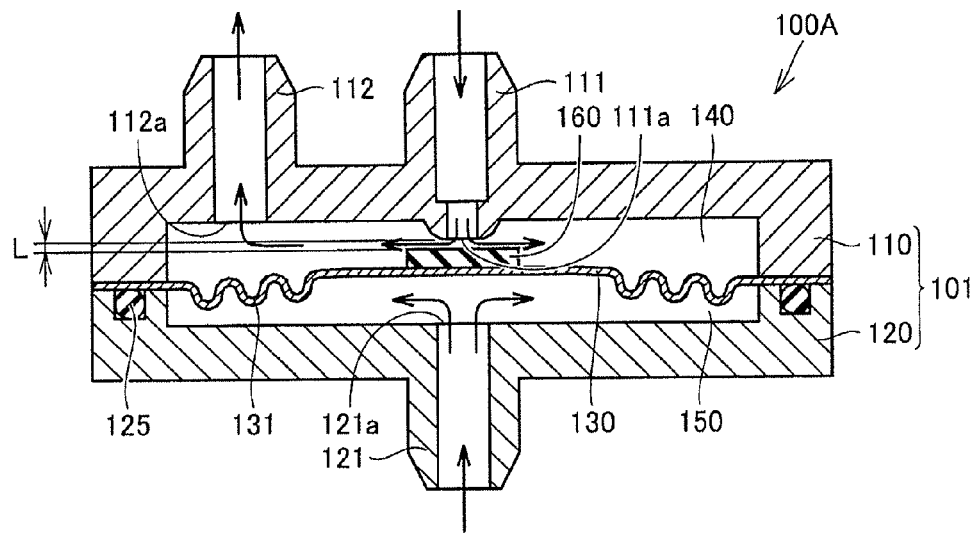
FIG. 5C is a schematic cross-sectional view showing an operating condition of the valve unit shown in FIG. 3.

FIGS. 4A and 4B are schematic cross-sectional views showing operating conditions of the aforementioned piezoelectric pump unit, and FIGS. 5A to 5C are schematic cross-sectional views showing operating conditions of the aforementioned valve unit. Next, with reference to FIGS. 4A to 5C, the operations of the piezoelectric pump unit 200A and the valve unit 100A will be described. It should be noted that in FIGS. 4A to 5C, the flow of air serving as the working medium and the flow of the compressed air are schematically indicated by arrows.

FIG. 4A shows a state in which the piezoelectric pump unit 200A is operated. In this operating state, a predetermined voltage is applied to the piezoelectric element 260 to cause the piezoelectric element 260 to vibrate, and as a result, the vibrating plate portion 232 vibrates in the direction of arrow B shown in FIG. 3.

At this time, as shown in FIG. 4A, airflow through the minute communication hole 231a provided in the thin plate portion 231 is generated between the surrounding space 250 and the pumping space 240. However, since the minute communication hole 231a is configured to be sufficiently small, a negative pressure will be continuously produced by the Venturi effect in a portion of the surrounding space 250 that faces the minute communication hole 231a. Moreover, since the ejection port 211a is disposed opposite to the minute communication hole 231a, the negative pressure causes air serving as the working medium to be continuously suctioned into the surrounding space 250 through the suction port 220a, and the suctioned air serving as the working medium will be continuously ejected through the ejection port 211a.

Thus, in the piezoelectric pump unit 200A that is in the operating state, the flow of air as shown in the drawing is continuously produced, and a pump function of continuously ejecting air serving as the working medium through the ejection port 211a will be exhibited.

FIG. 4B shows a state in which the piezoelectric pump unit 200A is stopped. In this stopped state, the vibrating plate portion 232 does not vibrate, and therefore the pump function as described above will not be exhibited as a matter of course.

Here, under a condition that the pressure (usually at atmospheric pressure) on the side of the suction port 220a of the piezoelectric pump unit 200A is lower than the pressure on the side of the ejection port 211a (i.e., the internal pressure of the working space 150 of the valve unit 100A connected to the ejection portion 211), the flow of air as shown in the drawing will be produced. In other words, air serving as the working medium will be suctioned into the surrounding space 250 through the ejection port 211a, and the suctioned air serving as the working medium will be ejected through the suction port 220a. That is to say, assuming that the direction of the flow of air shown in FIG. 4A is a forward direction, the flow of air in a reverse direction to the forward direction will be generated.

As described above, the piezoelectric pump unit 200A of this embodiment exhibits the pump function of increasing the internal pressure of the working space 150 of the valve unit 100A when it is operated, and exhibits an escape function of lowering the internal pressure of the working space 150 of the valve unit 100A to return to atmospheric pressure when it is stopped.

FIG. 5A shows a state in which the pressure on the side of the inlet port 111a of the valve unit 100A (i.e., the internal pressure of the compressing air bladder 42 connected to the inlet portion 111) is higher than atmospheric pressure and the piezoelectric pump unit 200A is stopped. In this state, since the piezoelectric pump unit 200A is not driven, the internal pressure of the working space 150 of the valve unit 100A is maintained at atmospheric pressure.

For this reason, the diaphragm 130 is not deflected toward the side of the flow space 140, the valve body 160 is positioned at a predetermined distance from the inlet port 111a, and the inlet port 111a is opened to be in a fully opened state. Accordingly, the compressed air flows into the flow space 140 through the inlet port 111a, and the compressed air flowing into the flow space 140 flows to the outside via the outlet port 112a.

FIGS. 5B and 5C show states in which the pressure on the side of the inlet port 111a of the valve unit 100A (i.e., the internal pressure of the compressing air bladder 42 connected to the inlet portion 111) is higher than atmospheric pressure and the piezoelectric pump unit 200A is driven at a predetermined output power.

In the state shown in FIG. 5B, the piezoelectric pump unit 200A is driven so as to generate a sufficiently high output power, and the internal pressure of the working space 150 of the valve unit 100A is maintained at a pressure that is sufficiently higher than atmospheric pressure. For this reason, a sufficiently large deflection toward the side of the flow space 140 occurs in the diaphragm 130, and the portion of the diaphragm 130 on which the valve body 160 is provided is displaced so that the inlet port 111a is completely closed by the valve body 160 to be in a fully closed state. Accordingly, the inflow of the compressed air through the inlet port 111a into the flow space 140 is completely blocked, and the internal pressure of the compressing air bladder 42 is maintained.

In the state shown in FIG. 5C, the piezoelectric pump unit 200A is driven so as to generate a somewhat high output power (however, an output power that is smaller than the output power generated in the state shown in FIG. 5B), and the internal pressure of the working space 150 of the valve unit 100A is maintained at a pressure that is somewhat higher than atmospheric pressure (i.e., a pressure that is smaller than the pressure in the state shown in FIG. 5B). For this reason, a somewhat large deflection (i.e., a deflection that is smaller than the deflection that occurs in the state shown in FIG. 5B) toward the side of the flow space 140 occurs in the diaphragm 130, and the portion of the diaphragm 130 on which the valve body 160 is provided is displaced so that the inlet port 111a is in a state in which it is closed to a certain extent by the valve body 160. Accordingly, although the compressed air flows into the flow space 140 through the inlet port 111a, and the compressed air flowing into the flow space 140 flows to the outside via the outlet port 112a, the inflow of the compressed air through the inlet port 111a into the flow space 140 is blocked to a certain extent by the valve body 160, and the flow rate of the compressed air flowing into the flow space 140 is reduced.

Here, distance L shown in FIG. 5C (i.e., the distance between the opening surface of the inlet port 111a and the principal surface of the valve body 160 that is on the side of the inlet port 111a) can be variably adjusted by controlling the magnitude of the driving voltage applied to the piezoelectric pump unit 200A. Thus, the flow rate of the compressed air flowing into the flow space 140 through the inlet port 111a can be variably adjusted by adjusting the distance L. Accordingly, the flow rate of the compressed air flowing out through the outlet port 112a can be variably adjusted by appropriately controlling the magnitude of the above-described driving voltage.

It should be noted that in order to maintain the internal pressure of the compressing air bladder 42, it is necessary to completely block the inflow of the compressed air through the inlet port 111a into the flow space 140 as described above. For this reason, in order to realize the state shown in FIG. 5B, it is an essential condition that the valve body 160 is larger than the inlet port 111a. In other words, it is necessary that the valve body 160 has a sufficient size to completely close the inlet port 111a in a state in which the above-described distance L is reduced to zero (i.e., a state in which L=0).

Figure 6:
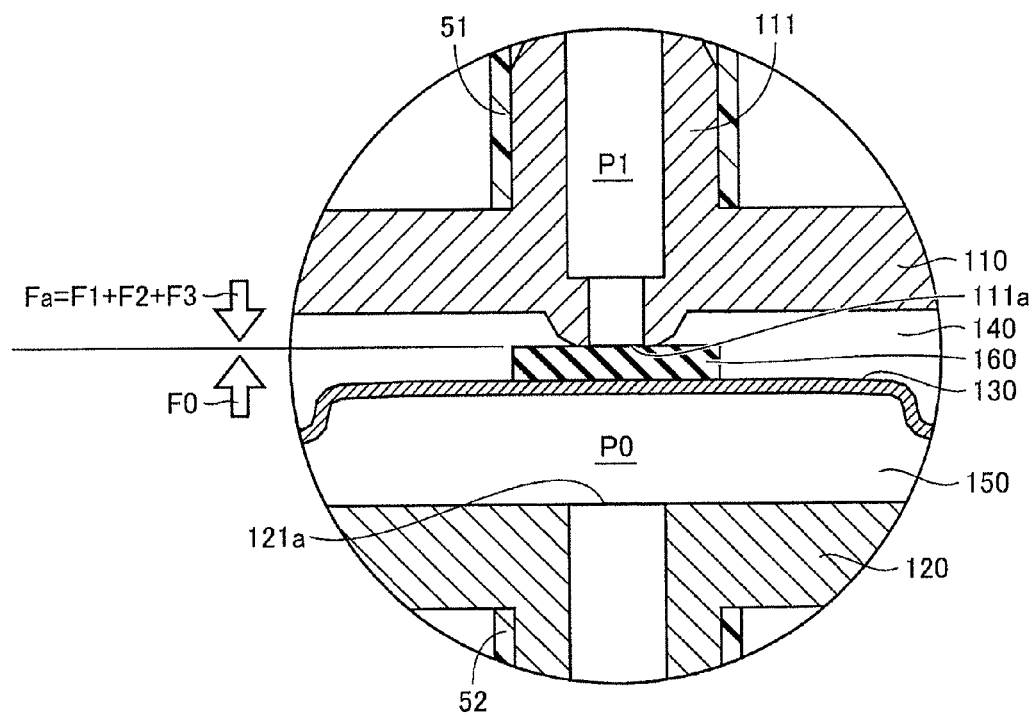
FIG. 6 is an enlarged cross-sectional view of a relevant portion of the valve unit shown in FIG. 3.

FIG. 6 is an enlarged cross-sectional view of a relevant portion of the valve unit of the flow rate control valve of this embodiment in the fully closed state. Next, with reference to FIG. 6, a pressure in the working space that is necessary for the inlet port 111a to be fully closed by the valve body 160 will be described in light of the specifications of a standard sphygmomanometer.

With reference to FIG. 6, as a thrust F0 [N] that is necessary for the inlet port 111a to be fully closed by the valve body 160 against the internal pressure of the compressing air bladder 42 (i.e., the cuff pressure), a force is required that is greater than or equal to a drag force Fa [N] that is the sum total of a reaction force F1 [N] against the cuff pressure P1 [mmHg], a deformation reaction force F2 [N] of the valve body 160 that is made of an elastic body and pressed against the periphery of the inlet port 111a, and a deformation reaction force F3 [N] of the deflected diaphragm 130. Thus, when the inner diameter of the inlet port 111a is $\phi 1$ [cm], formulae (1) to (3) below hold.

$$Fa = F1 + F2 + F3 \quad (1)$$

$$F0 > Fa \quad (2)$$

$$F1 = P1 \times 1.332 \times 10^{-2} \times \pi \times \phi 1^2 / 4 \quad (3)$$

Here, in light of the specifications of a standard sphygmomanometer, when the cuff pressure P1 is set at 400 [mmHg], and the inner diameter $\phi 1$ of the inlet port 111a is set at, for example, 0.16 [cm], the reaction force F1 is $1.09 \times 10^{-1}$ [N] from the above-described formula (3).

Moreover, in light of the material characteristics of a standard valve body 160 and diaphragm 130, when the reaction force F2 is set at $2 \times 10^{-2}$ [N], and the reaction force F3 is set at $1.32 \times 10^{-1}$ [N], the drag force Fa is $2.61 \times 10$ [N]=26.6 [g] from the above-described formula (1).

Therefore, taking a certain amount of leeway into account based on the above-described formula (2), it is assumed that the thrust F0 [N] is required to be about $3.0 \times 10^{-1}$ [N].

It should be noted that the internal pressure P0 [mmHg] of the working space 150 that is required to generate the thrust F0 of about $3.0 \times 10^{-1}$ [N] is calculated from a relation P0=F0/$(1.332 \times 10^{-2} \times \pi \times \phi 0^2 / 4)$, where the inner diameter of a portion of the diaphragm 130 that faces the working space 150 is $\phi 0$ [cm], and is 7.2 [mmHg].

From the foregoing results, when the area of a portion of the diaphragm 130 that is displaced in accordance with a change in the internal pressure of the working space 150 is made sufficiently larger than the opening area of the inlet port 111a, the output power that the piezoelectric pump unit 200A is required to generate in order for the inlet port 111a to be fully closed by the valve body 160 can be low, and thus the power consumption can be significantly reduced. It should be noted that both of the opening area of the inlet port 111a and the area of that portion of the diaphragm 130 that is displaced in accordance with a change in the internal pressure of the working space 150 can be changed variously and can be optimized according to the specifications.

Next, effects of providing the valve body 160 on the diaphragm 130 of the flow rate control valve 32A of this embodiment will be described.

In order to secure a wider adjustment range of the flow rate of the compressed air, it is required that the amount of deflection of the diaphragm 130 changes more sensitively with a change in the internal pressure of the working space 150. For this purpose, the diaphragm 130 is composed of a thin film as described above so that it is more likely to be deflected. However, the thinner the film that constitutes the diaphragm 130, the smaller the rigidity. Therefore, the diaphragm 130 will be likely to be locally deformed.

Here, if a configuration is employed in which the inlet port 111a is closed by the diaphragm 130 directly coming into contact with it, instead of providing the valve body 160 on the diaphragm 130, the difference between the pressure of the compressed air and the pressure in the working space 150 will cause a portion of the diaphragm 130 that opposes the inlet port 111a to be locally deflected. This results in a problem that it is difficult to precisely control the distance between the inlet port 111a and the portion of the diaphragm 130 that opposes the inlet port 111a by changing the internal pressure of the working space 150. Typically, in the case where the internal pressure of the working space 150 is reduced in a state in which the inlet port 111a is fully closed by the diaphragm 130, a phenomenon will occur in which the flow rate of the compressed air may immediately increase due to the occurrence of the above-described local deformation, and minute control of the flow rate of the compressed air will no longer be possible.

In contrast, like the aforementioned flow rate control valve 32A of this embodiment, when the valve body 160 made of a member that is harder than the diaphragm 130 is provided on the diaphragm 130, the rigidity of the portion of the diaphragm 130 on which the valve body 160 is provided is increased, and the occurrence of the aforementioned local deformation in that portion can be suppressed. Consequently, it is possible to precisely control the distance (i.e., the above-described distance L) between the valve body 160 and the inlet port 111a by changing the internal pressure of the working space 150. Typically, in the case where the internal pressure of the working space 150 is reduced in the state in which the inlet port 111a is fully closed by the valve body 160, the above-described local deformation does not occur, so that the flow rate of the compressed air can be more minutely increased, and minute control of the flow rate of the compressed air can be precisely performed.

Figure 7:
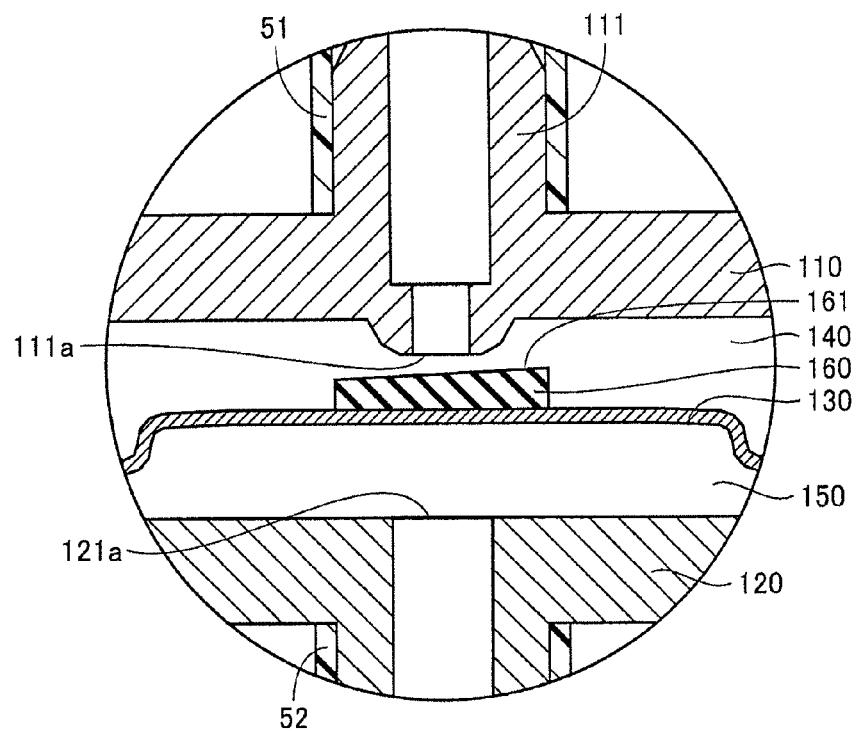
FIG. 7 is an enlarged cross-sectional view of a relevant portion showing another configuration example of the valve unit shown in FIG. 3.

FIG. 7 is an enlarged cross-sectional view of a relevant portion showing another configuration example of the valve unit of the flow rate control valve of this embodiment. With regard to the valve unit 100A shown in FIG. 6, a case where the principal surface of the valve body 160 that closes the inlet port 111a is configured to be parallel to the opening surface of the inlet port 111a was described as an example. However, as in the case of the valve unit shown in FIG. 7, it is also possible to incline the principal surface of the valve body 160 that closes the inlet port 111a to configure the principal surface as an inclined surface 161 that is not parallel to the opening surface of the inlet port 111a.

Here, when the configuration as shown in FIG. 6 is employed, although the driving voltage of the piezoelectric pump unit 200A that is necessary for the inlet port 111a to be fully closed can be reduced, a problem arises in that the inflow of the compressed air significantly changes with respect to a change in the above-described driving voltage, and in some cases, it may be difficult to precisely control the flow rate control of the compressed air. However, when a configuration as shown in FIG. 7 is employed, even though the driving voltage of the piezoelectric pump unit 200A that is necessary for the inlet port 111a to be fully closed slightly increases, the change in the inflow of the compressed air with respect to a change in the above-described driving voltage decreases, and thus there is an advantage that precise flow rate control of the compressed air can be performed more easily.

The reason for this is that the employment of this configuration makes it possible to perform precise control among the following states in accordance with the amount of displacement of the portion of the diaphragm 130 on which the valve body 160 is provided: a state in which the valve body 160 is elastically deformed as a result of coming into contact with peripheral edges of the inlet port 111a and is in close contact with the peripheral edges to fully close the inlet port 111a; a state in which the valve body 160 is not in contact with the peripheral edges of the inlet port 111a, and the inlet port 111a and the flow space 140 are in communication with each other over a relatively wide area; and an intermediate state between these states, in which the inlet port 111a is not fully closed while the valve body 160 is in contact with the above-described peripheral edges, and the inlet port 111a and the flow space 140 are in communication with each other over a relatively narrow area.

It should be noted that in addition to the configuration as shown in FIG. 7, various configurations for facilitating precise flow rate control are conceivable, including a configuration in which the opening surface of the inlet port 111a is inclined, a configuration in which the diaphragm 130 is arranged at a tilt relative to the opening surface of the inlet port 111a to make the moving direction of the valve body 160 cross the normal direction of the opening surface of the inlet port 111a, and the like.

Figure 8:
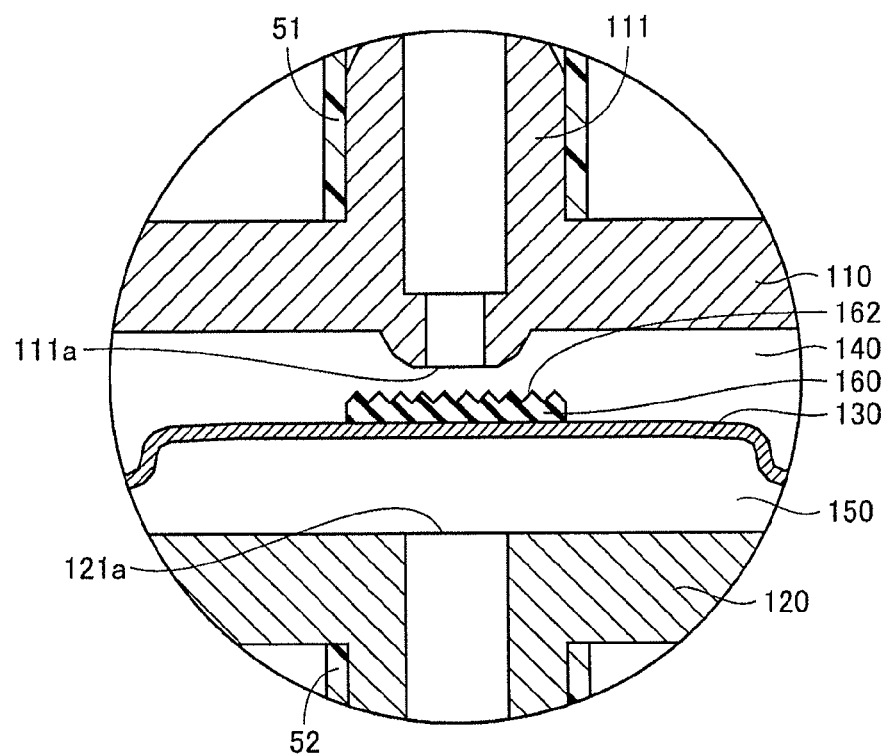
FIG. 8 is an enlarged cross-sectional view of a relevant portion showing still another configuration example of the valve unit shown in FIG. 3.

FIG. 8 is an enlarged cross-sectional view of a relevant portion showing still another configuration example of the valve unit of the flow rate control valve of this embodiment. With regard to the valve unit 100A shown in FIG. 6, a case where the principal surface of the valve body 160 that closes the inlet port 111a is composed of a flat surface was described as an example. However, as in the case of a valve unit shown in FIG. 8, the principal surface may also be composed of a non-flat surface by providing minute protrusions and recesses 162 in the principal surface. With this configuration, precise flow rate control can be easily performed as well.

That is to say, in the case where a configuration is employed in which minute protrusions and recesses are provided in the principal surface of the valve body 160 that opposes the inlet port 111a, precise control among the following states can be performed in accordance with the amount of displacement of the portion of the diaphragm 130 on which the valve body 160 is provided: a state in which the valve body 160 is elastically deformed as a result of coming into contact with the peripheral edges of the inlet port 111a, so that protrusions of the minute protrusions and recesses are deformed by compression to allow the valve body 160 to be in close contact with the peripheral edges, and thus the inlet port 111a is fully closed; a state in which the valve body 160 is not in contact with the peripheral edges of the inlet port 111a, and the inlet port 111a and the flow space 140 are in communication with each other over a relatively wide area; and an intermediate state between these states, in which the inlet port 111a is not fully closed while protrusions of the minute protrusions and recesses are in contact with the above-described peripheral edges, and the inlet port 111a and the flow space 140 are in communication with each other over a relatively narrow area. Therefore, precise flow rate control can be more easily performed.

Figure 9:
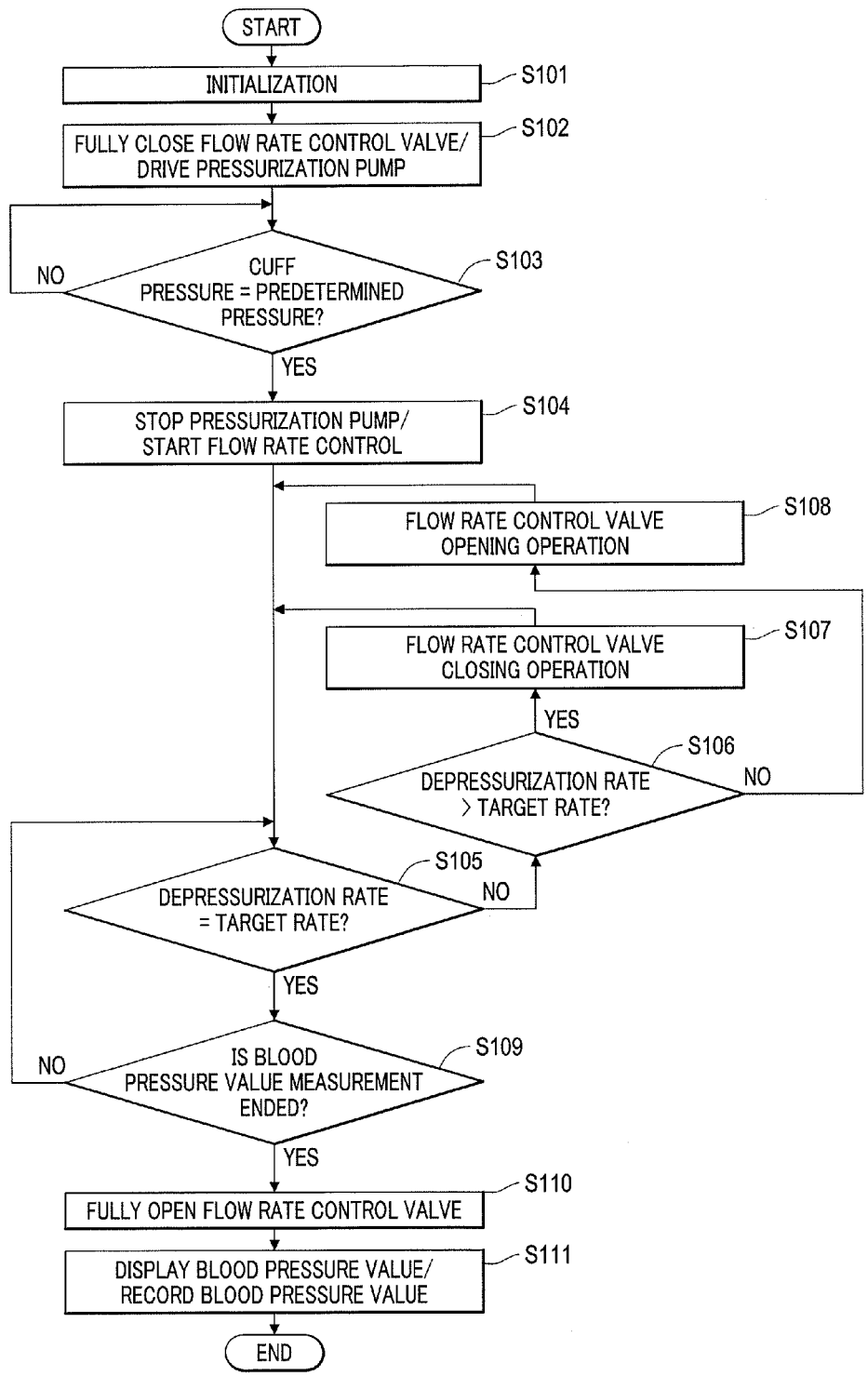
FIG. 9 is a diagram illustrating an operation flow based on a depressurization measurement method of the sphygmomanometer of Embodiment 1 of the invention.
Figure 10:
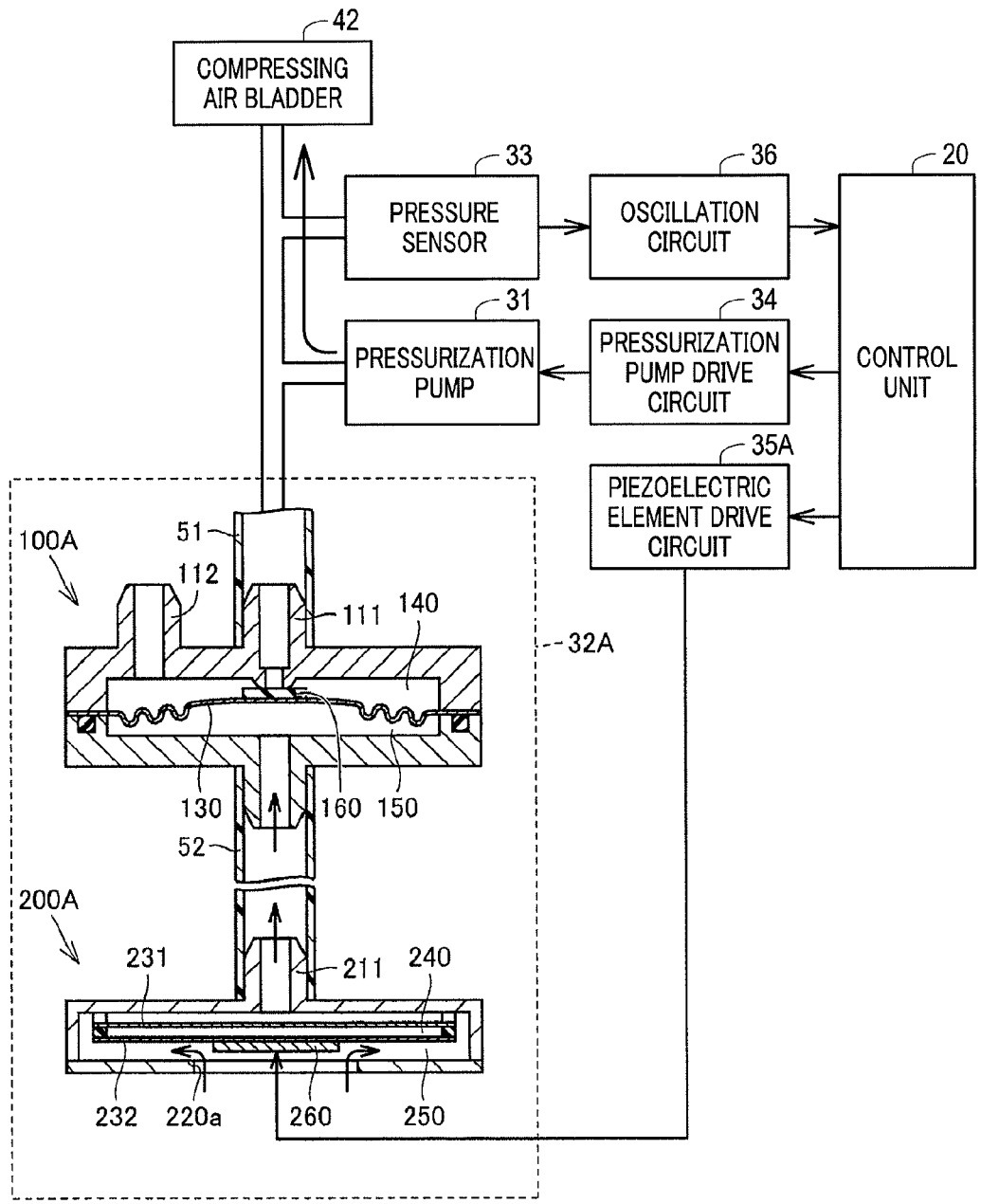
FIG. 10 is a diagram illustrating a specific operation of the sphygmomanometer of Embodiment 1 of the invention in a quick pressurization process according to the operation flow illustrated in FIG. 9.
Figure 11:
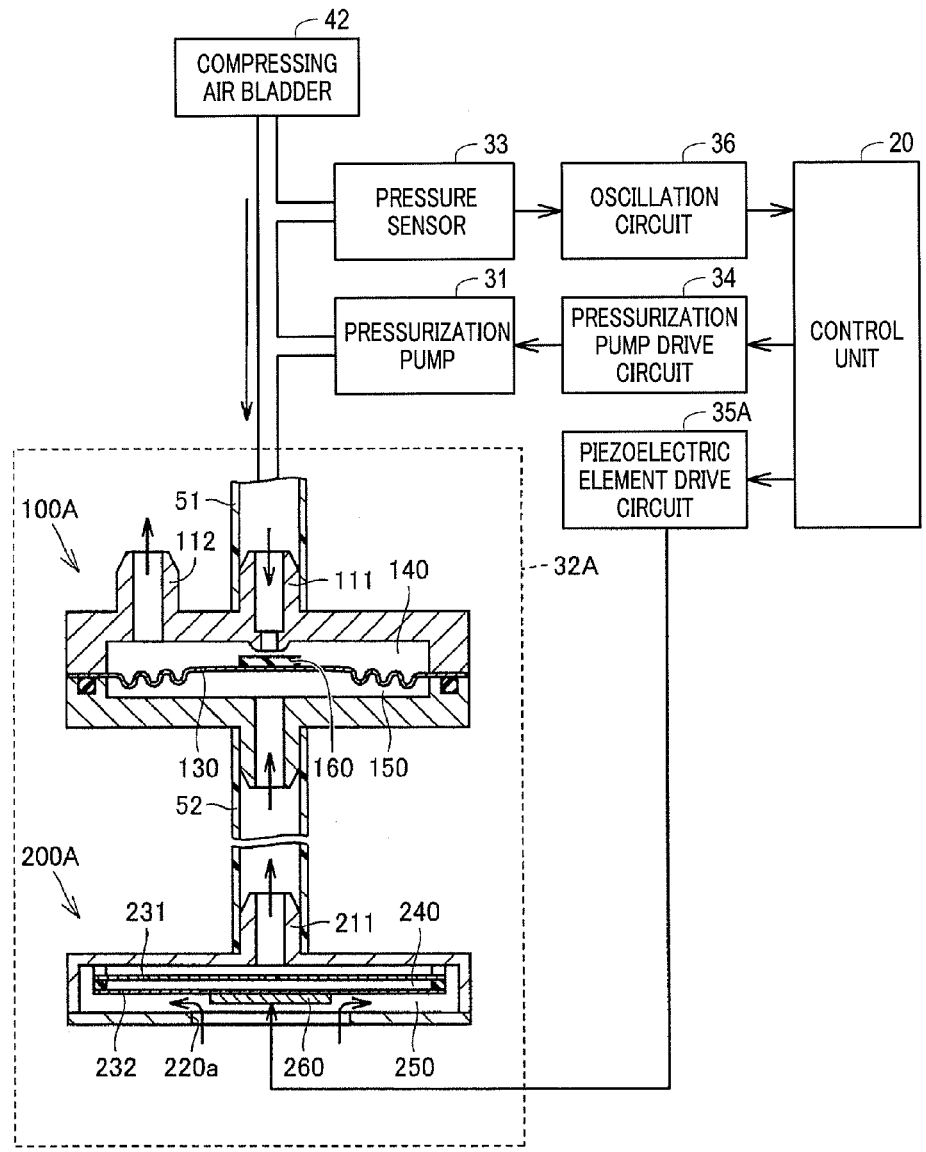
FIG. 11 is a diagram illustrating a specific operation of the sphygmomanometer of Embodiment 1 of the invention in a slow depressurization process according to the operation flow illustrated in FIG. 9.
Figure 12:
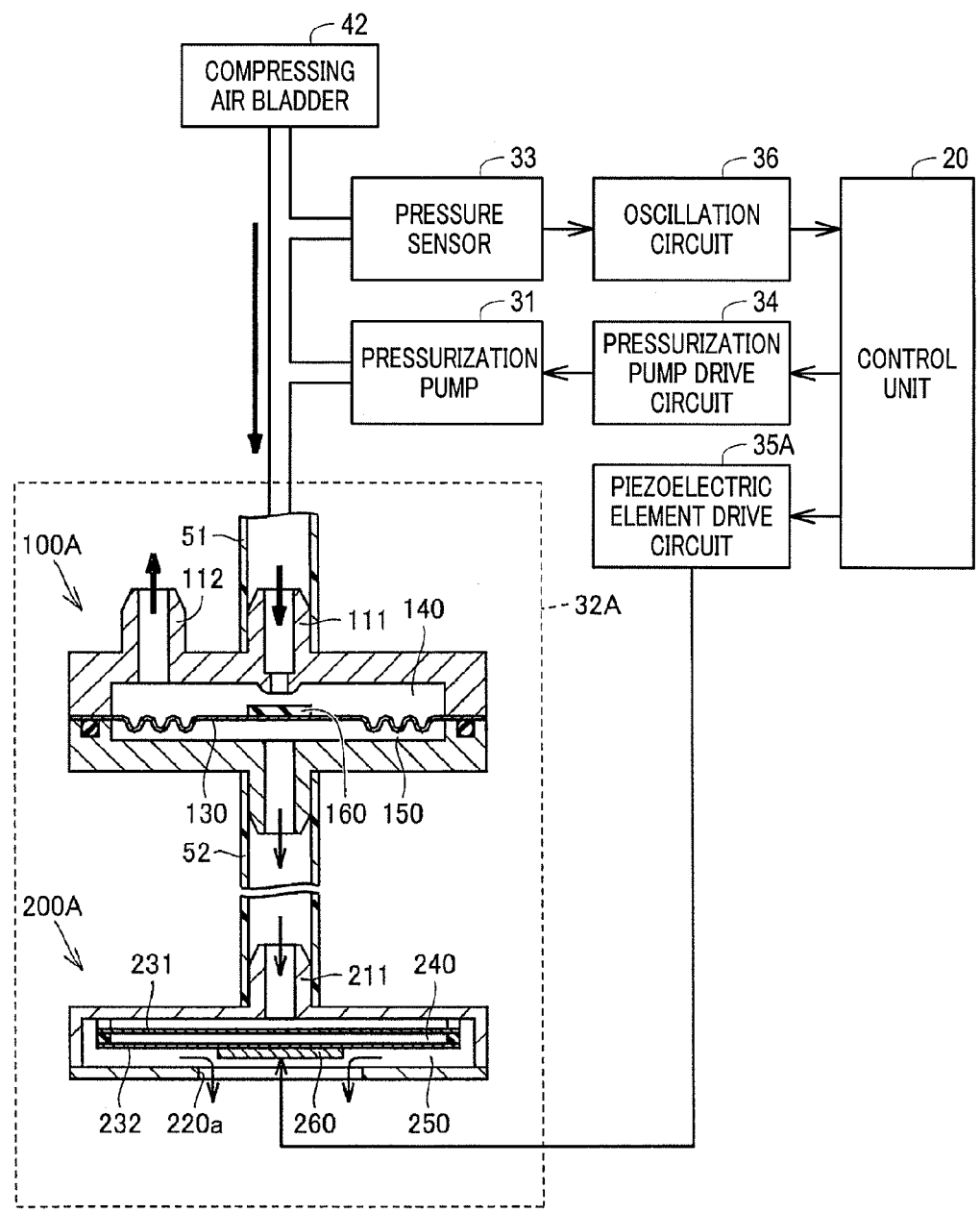
FIG. 12 is a diagram illustrating a specific operation of the sphygmomanometer of Embodiment 1 of the invention in a quick depressurization process according to the operation flow illustrated in FIG. 9.
Figure 13:
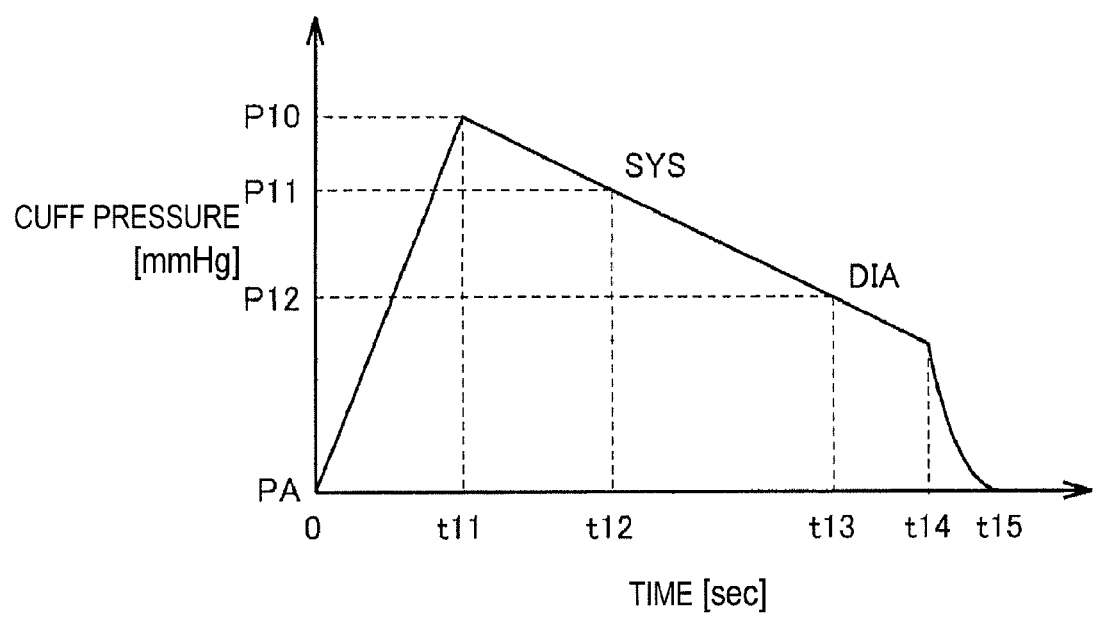
FIG. 13 is a graph showing a change over time in the internal pressure of a compressing air bladder according to the operation flow illustrated in FIG. 9.

FIG. 9 is a diagram illustrating an operation flow based on a depressurization measurement method of the sphygmomanometer of this embodiment, and FIGS. 10 to 12 are diagrams illustrating specific operations of the sphygmomanometer in a quick pressurization process, a slow depressurization process, and a quick depressurization process according to the operation flow illustrated in FIG. 9. Moreover, FIG. 13 is a graph showing a change over time in the internal pressure of the compressing air bladder according to the operation flow illustrated in FIG. 9. Next, with reference to FIGS. 9 to 13, specific operations and the like of the sphygmomanometer 1 in the case where a blood pressure value is measured on the sphygmomanometer 1 of this embodiment based on the depressurization measurement method will be described. It should be noted that a program conforming to the flow diagram illustrated in FIG. 9 is stored in the memory unit 22 in advance, and processing thereof is performed by the control unit 20 reading out the program from the memory unit 22 and executing the program.

During measurement of a blood pressure value based on the depressurization measurement method, the subject wraps the cuff 40 around the upper arm in advance, and, in this state, operates the operation unit 23 provided in the main body 10 to turn on the power to the sphygmomanometer 1. Thus, electric power is supplied from the power supply unit 24 to the control unit 20 to activate the control unit 20. As illustrated in FIG. 9, after being activated, firstly, the control unit 20 initializes the sphygmomanometer 1 (step S101).

Then, as illustrated in FIG. 9, the control unit 20 waits for an instruction from the subject to start measurement, and if the subject gives an instruction to start measurement by operating the operation unit 23, the control unit 20 fully closes the flow rate control valve 32A and drives the pressurization pump 31 to increase the cuff pressure of the compressing air bladder 42 (step S102).

Specifically, as illustrated in FIG. 10, the control unit 20 gives a predetermined control signal to the pressurization pump drive circuit 34 to drive the pressurization pump 31 to feed the compressed air from the pressurization pump 31 to the compressing air bladder 42, and also gives a predetermined control signal to the piezoelectric element drive circuit 35A to drive the piezoelectric pump unit 200A to introduce air serving as the working medium into the working space 150 of the valve unit 100A, thereby deflecting the diaphragm 130 to move the valve body 160 so that the inlet port 111a is fully closed by the valve body 160. The driving voltage applied to the piezoelectric element 260 at this time is set to a magnitude of voltage that is sufficient to enable the valve body 160 to fully close the inlet port 111a.

Step S102 described above corresponds to the quick pressurization process in which the compressing air bladder 42 is pressurized at a relatively high pressurization rate. That is to say, as shown in FIG. 13, in this quick pressurization process, the cuff pressure increases in conformity with a predetermined pressurization rate (see time 0 to t11), and the compressing air bladder 42 is inflated accordingly, so that the upper arm of the subject is compressed.

Then, as illustrated in FIG. 9, the control unit 20 determines whether or not the cuff pressure has reached a predetermined pressure that was specified in advance (step S103). If it is determined that the cuff pressure has not yet reached the predetermined pressure (NO in step S103), the control unit 20 continues driving the pressurization pump 31, and if it is determined that the cuff pressure has reached the predetermined pressure (YES in step S103), the control unit 20 stops the pressurization pump 31 and starts controlling the discharge flow rate of the compressed air by means of the flow rate control valve 32A (step S104). Here, a pressure that is higher than a common systolic blood pressure value like a cuff pressure P10 (the cuff pressure at time t11) shown in FIG. 13 is used as the above-described predetermined pressure.

Specifically, as illustrated in FIG. 11, the control unit 20 gives a predetermined control signal to the pressurization pump drive circuit 34 to stop the pressurization pump 31, and also gives a predetermined control signal to the piezoelectric element drive circuit 35A to continue driving of the piezoelectric pump unit 200A at a lowered output power, thereby reducing the internal pressure of the working space 150 to reduce the deflection of the diaphragm 130 to move the valve body 160 so that the inlet port 111a is slightly opened. As a result, the compressed air that is present inside the compressing air bladder 42 is gradually discharged via the flow rate control valve 32A. The driving voltage applied to the piezoelectric element 260 at this time is a voltage that is smaller than a magnitude of voltage that is sufficient to enable the valve body 160 to fully close the inlet port 111a, and that falls within a range that can restrict the flow rate of the compressed air flowing in through the inlet port 111a to a predetermined flow rate.

Here, the control of the discharge flow rate of the compressed air is performed based on a change in the cuff pressure detected by the pressure sensor 33.

More specifically, as illustrated in FIG. 9, the control unit 20 determines whether or not the depressurization rate of the cuff pressure matches a target rate that was specified in advance, based on a change in the cuff pressure detected by the pressure sensor 33 (step S105). If it is determined that the depressurization rate of the cuff pressure does not match the target rate that was specified in advance (NO in step S105), the control unit 20 determines whether or not the depressurization rate is greater than the target rate (step S106). If it is determined that the depressurization rate is greater than the target rate (YES in step S106), the control unit 20 slightly increases the driving voltage to the flow rate control valve 32A to move the valve body 160 in a closing direction to slow down the depressurization rate (step S107). If it is determined that the depressurization rate is less than the target rate (NO in step S106), the control unit 20 slightly reduces the driving voltage to the flow rate control valve 32A to move the valve body 160 in an opening direction to speed up the depressurization rate (step S108). Afterward, in both cases, the control unit 20 continues controlling the discharge flow rate of the compressed air (return to step S105).

Moreover, if it is determined that the depressurization rate of the cuff pressure matches the target rate specified in advance (YES in step S105), the control unit 20 determines whether or not the blood pressure value measurement is ended (step S109), and if it is determined that the blood pressure value measurement is not ended (NO in step S109), the control unit 20 continues controlling the discharge flow rate of the compressed air (return to step S105). It should be noted that preferably, a predetermined constant depressurization rate is employed as the above-described target rate.

Steps S105 to S109 described above correspond to the slow depressurization process in which the compressing air bladder 42 is gradually depressurized. That is to say, as shown in FIG. 13, in this slow depressurization process, the cuff pressure gradually decreases in conformity with the target rate specified in advance (see time t11 to time t14), and accordingly, the compressing air bladder 42 is gradually deflated.

In the slow depressurization process, the control unit 20 calculates blood pressure values using a known procedure. Specifically, the control unit 20 extracts pulse wave information based on an oscillation frequency obtained from the oscillation circuit 36, and calculates a systolic blood pressure value and a diastolic blood pressure value based on the extracted pulse wave information. Thus, as shown in FIG. 13, first, the systolic blood pressure value (SYS) is calculated as a cuff pressure P11 at time t12, and then the diastolic blood pressure value (DIA) is calculated as a cuff pressure P12 at time t13.

As illustrated in FIG. 9, if it is determined that the blood pressure value measurement is ended (YES in step S109), the control unit 20 fully opens the flow rate control valve 32A to quickly discharge the compressed air, thereby lowering the cuff pressure (step S110).

Specifically, as illustrated in FIG. 12, the control unit 20 gives a predetermined control signal to the piezoelectric element drive circuit 35A to stop the piezoelectric pump unit 200A, thereby releasing air serving as the working medium from the working space 150 of the valve unit 100A to reduce the deflection of the diaphragm 130 to move the valve body 160 so that the inlet port 111a is brought into a fully opened state. As a result, the compressed air that is present inside the compressing air bladder 42 is quickly discharged via the flow rate control valve 32A.

Step S110 described above corresponds to the quick depressurization process in which the compressing air bladder 42 is quickly depressurized. That is to say, as shown in FIG. 13, in this quick depressurization process, the cuff pressure quickly decreases to atmospheric pressure PA at a predetermined depressurization rate (see time t14 to time t15), and accordingly, the compressing air bladder 42 is completely deflated, so that compression of the upper arm of the subject is removed.

Then, as illustrated in FIG. 9, the control unit 20 displays the blood pressure values as a measurement result on the display unit 21 and stores those blood pressure values in the memory unit 22 (step S111). Afterward, the control unit 20 ends the operation after receiving an instruction from the subject to turn off the power.

Figure 14:
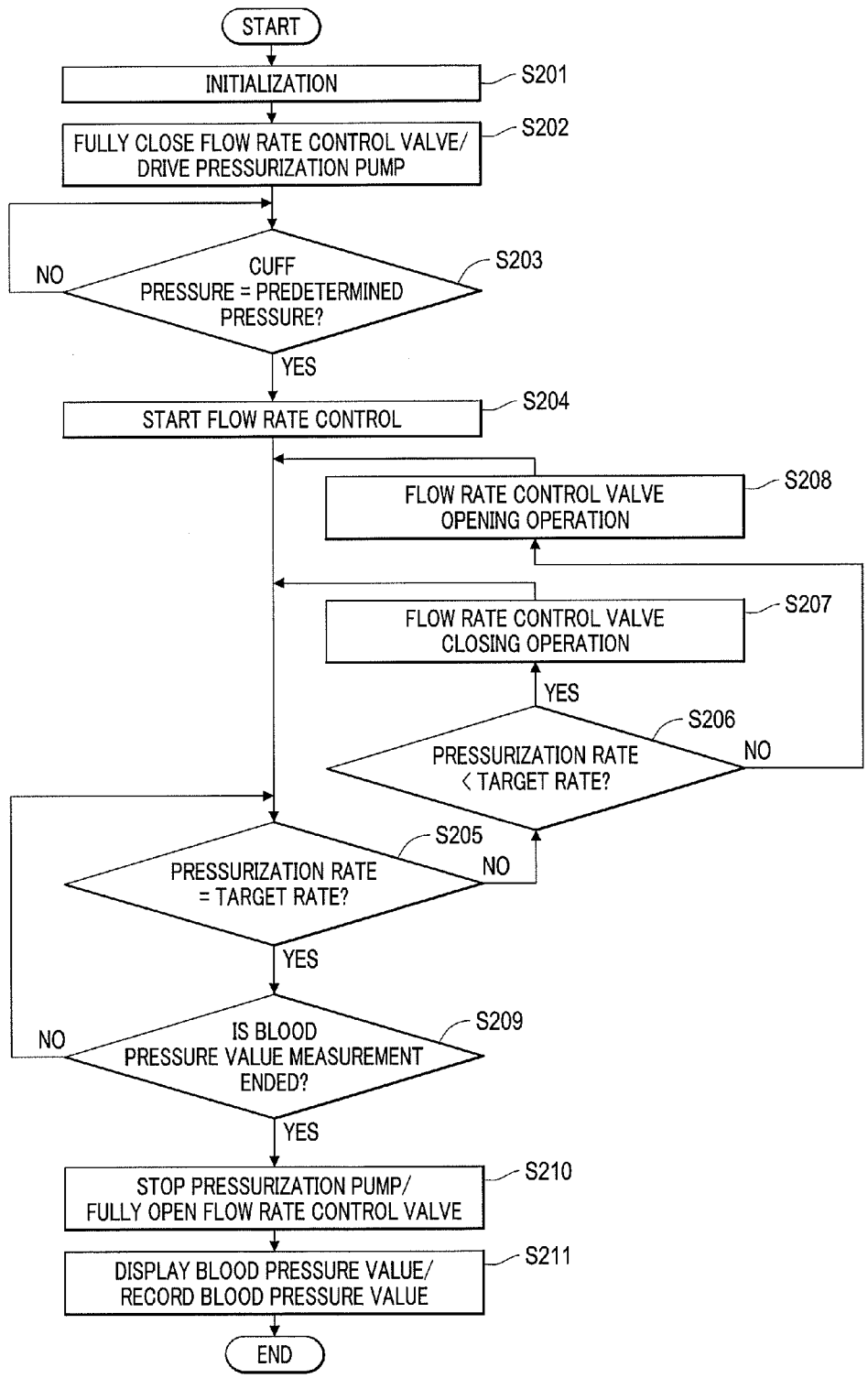
FIG. 14 is a diagram illustrating an operation flow based on a pressurization measurement method of the sphygmomanometer of Embodiment 1 of the invention.
Figure 15:
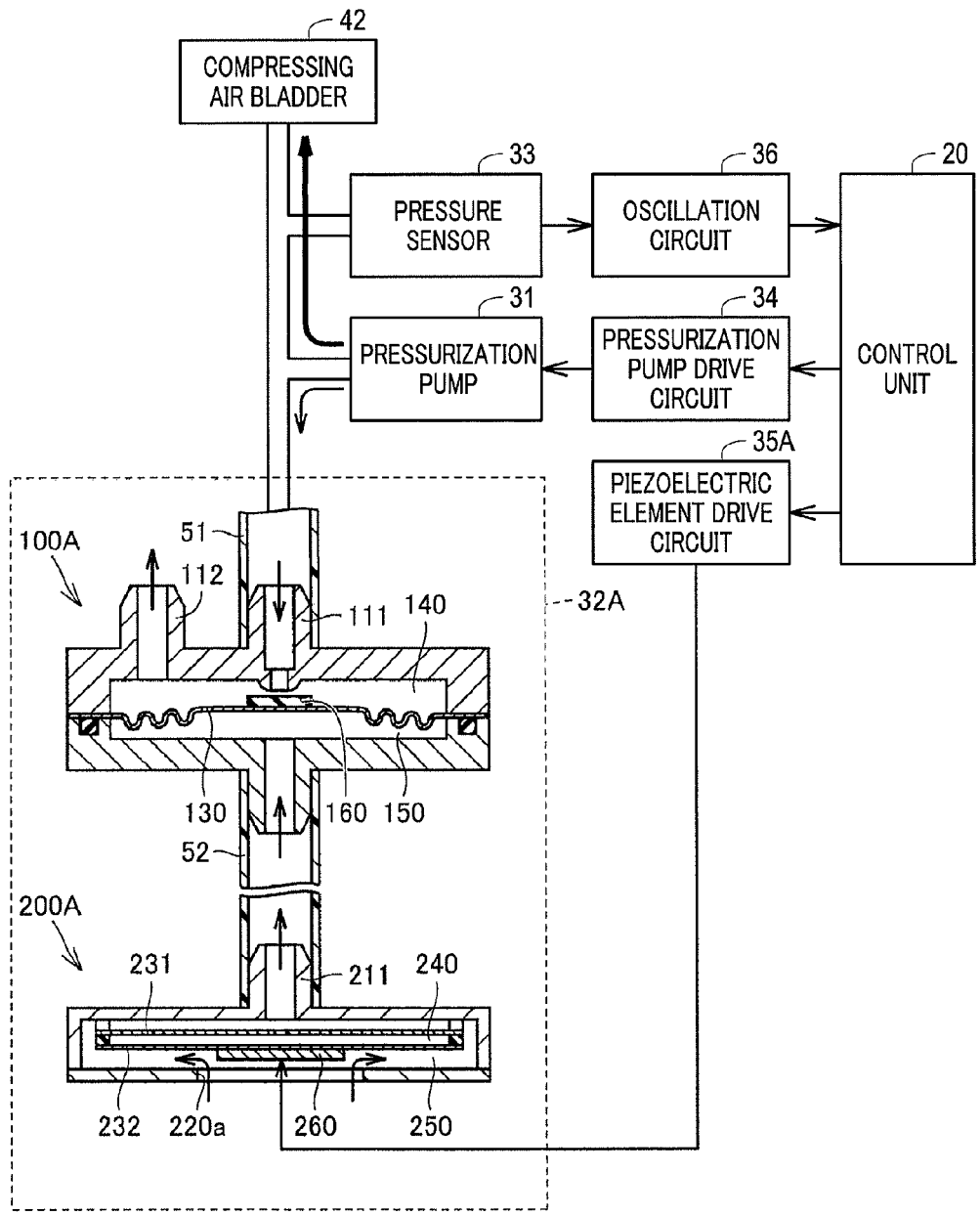
FIG. 15 is a diagram illustrating a specific operation of the sphygmomanometer of Embodiment 1 of the invention in a slow pressurization process according to the operation flow illustrated in FIG. 14.
Figure 16:
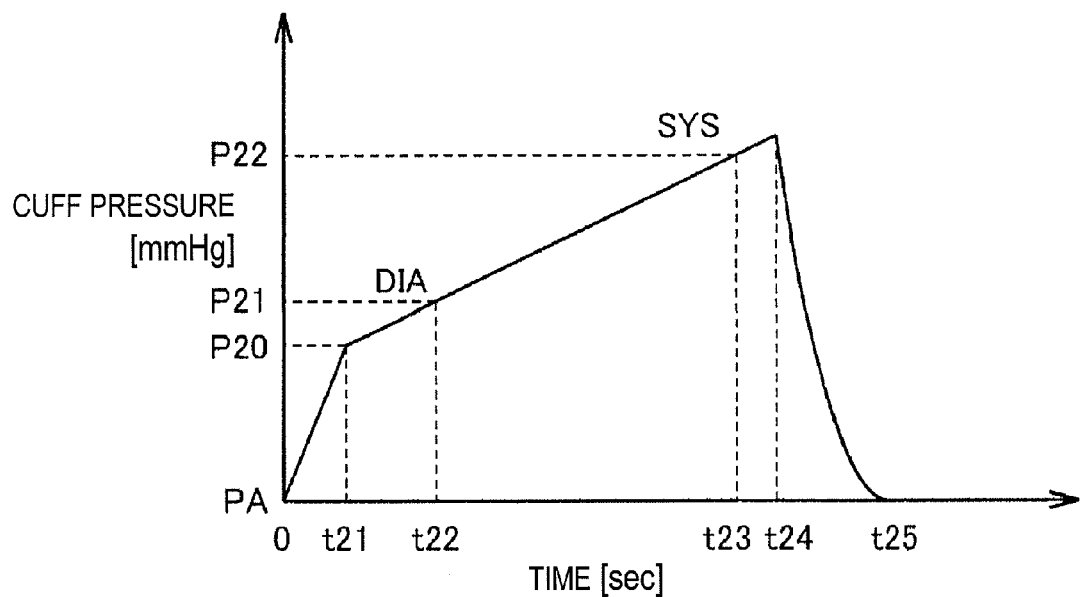
FIG. 16 is a graph showing a change over time in the internal pressure of the compressing air bladder according to the operation flow illustrated in FIG. 14.

FIG. 14 is a diagram illustrating an operation flow based on a pressurization measurement method of the sphygmomanometer of this embodiment, and FIG. 15 is a diagram illustrating a specific operation of the sphygmomanometer in a slow pressurization process according to the operation flow illustrated in FIG. 14. Moreover, FIG. 16 is a graph showing a change over time in the internal pressure of the compressing air bladder according to the operation flow illustrated in FIG. 14. Next, with reference to FIGS. 14 to 16, specific operations and the like of the sphygmomanometer 1 in the case where a blood pressure value is measured on the sphygmomanometer 1 of this embodiment based on the pressurization measurement method will be described. It should be noted that a program conforming to the flow diagram illustrated in FIG. 14 is stored in the memory unit 22 in advance, and processing thereof is performed by the control unit 20 reading out this program from the memory unit 22 and executing the program.

During measurement of a blood pressure value based on the pressurization measurement method, the subject wraps the cuff 40 around the upper arm in advance and, in this state, operates the operation unit 23 provided in the main body 10 to turn on the power to the sphygmomanometer 1. Thus, electric power is supplied from the power supply unit 24 to the control unit 20 to activate the control unit 20. As illustrated in FIG. 14, after being activated, firstly, the control unit 20 initializes the sphygmomanometer 1 sphygmomanometer (step S201).

Then, as illustrated in FIG. 14, the control unit 20 waits for an instruction from the subject to start measurement. If the subject gives an instruction to start measurement by operating the operation unit 23, the control unit 20 fully closes the flow rate control valve 32A and drives the pressurization pump 31 to increase the cuff pressure of the compressing air bladder 42 (step S202). It should be noted that specific operations of the sphygmomanometer 1 at this time are the same as the operations illustrated in FIG. 10, and so descriptions thereof are not repeated here.

Step S202 described above corresponds to a quick pressurization process in which the compressing air bladder 42 is pressurized at a relatively high pressurization rate. That is to say, as shown in FIG. 16, in this quick pressurization process, the cuff pressure increases in conformity with a predetermined pressurization rate (see time 0 to t21), and accordingly the compressing air bladder 42 is inflated, so that the upper arm of the subject is compressed.

Then, as illustrated in FIG. 14, the control unit 20 determines whether or not the cuff pressure has reached a predetermined pressure that was specified in advance (step S203). If it is determined that the cuff pressure has not yet reached the predetermined pressure (NO in step S203), the control unit 20 continues driving the pressurization pump 31, and if it is determined that the cuff pressure has reached the predetermined pressure (YES in step S203), the control unit 20 starts controlling the discharge flow rate of the compressed air by means of the flow rate control valve 32A (step S204). Here, a pressure that is lower than a common diastolic blood pressure value like a cuff pressure P20 (the cuff pressure at time t21) shown in FIG. 16 is used as the above-described predetermined pressure.

Specifically, as illustrated in FIG. 15, the control unit 20 gives a predetermined control signal to the piezoelectric element drive circuit 35A to continue driving the piezoelectric pump unit 200A at a lowered output power, thereby reducing the internal pressure of the working space 150 to reduce the deflection of the diaphragm 130 to move the valve body 160 so that the inlet port 111a is slightly opened. As a result, a part of the compressed air fed from the pressurization pump 31 to the compressing air bladder 42 is discharged via the flow rate control valve 32A. The driving voltage applied to the piezoelectric element 260 at this time is a voltage that is lower than a magnitude of voltage that is sufficient to enable the valve body 160 to fully close the inlet port 111a, and that falls within a range that can restrict the flow rate of the compressed air entering through the inlet port 111a to a predetermined flow rate.

Here, the control of the discharge flow rate of the compressed air is performed based on a change in the cuff pressure detected by the pressure sensor 33.

More specifically, as illustrated in FIG. 14, the control unit 20 determines whether or not the pressurization rate of the cuff pressure matches a target rate that was specified in advance, based on a change in the cuff pressure detected by the pressure sensor 33 (step S205). If it is determined that the pressurization rate of the cuff pressure does not match the target rate specified in advance (NO in step S205), the control unit 20 determines whether or not the pressurization rate is less than the target rate (step S206). If it is determined that the pressurization rate is less than the target rate (YES in step S206), the control unit 20 slightly increases the driving voltage to the flow rate control valve 32A to move the valve body 160 in the closing direction to speed up the pressurization rate (step S207). If it is determined that the pressurization rate is greater than the target rate (NO in step S206), the control unit 20 slightly decreases the driving voltage to the flow rate control valve 32A to move the valve body 160 in the opening direction to slow down the pressurization rate (step S208). In both cases, afterward, the control unit 20 continues controlling the discharge flow rate of the compressed air (return to step S205).

Moreover, if it is determined that the pressurization rate of the cuff pressure matches the target rate specified in advance (YES in step S205), the control unit 20 determines whether or not the blood pressure value measurement is ended (step S209). If it is determined that the blood pressure value measurement is not ended (NO in step S209), the control unit 20 continues controlling the discharge flow rate of the compressed air (return to step S205). It should be noted that preferably, a predetermined constant pressurization rate is employed as the above-described target rate.

Steps S205 to S209 described above correspond to the slow pressurization process in which the compressing air bladder 42 is gradually pressurized. That is to say, as shown in FIG. 16, in this slow pressurization process, the cuff pressure gradually increases in conformity with the target rate specified in advance (see time t21 to time t24), and accordingly the compressing air bladder 42 is gradually inflated.

In the slow pressurization process, the control unit 20 calculates blood pressure values using a known procedure. Specifically, the control unit 20 extracts pulse wave information based on an oscillation frequency obtained from the oscillation circuit 36, and calculates a systolic blood pressure value and a diastolic blood pressure value based on the extracted pulse wave information. Thus, as shown in FIG. 16, first, a diastolic blood pressure value (DIA) is calculated as a cuff pressure P21 at time t22, and then a systolic blood pressure value (SYS) is calculated as a cuff pressure P22 at time t23.

As illustrated in FIG. 14, if it is determined that the blood pressure value measurement is ended (YES in step S209), the control unit 20 stops the pressurization pump 31 and fully opens the flow rate control valve 32A to quickly discharge the compressed air, thereby lowering the cuff pressure (step S210). It should be noted that specific operations of the sphygmomanometer 1 at this time are the same as the operations illustrated in FIG. 12 above, and so descriptions thereof are not repeated here.

Step S210 described above corresponds to a quick depressurization process in which the compressing air bladder 42 is quickly depressurized. That is to say, as shown in FIG. 16, in this quick depressurization process, the cuff pressure quickly decreases to atmospheric pressure PA at a predetermined depressurization rate (see time t24 to time t25), and accordingly the compressing air bladder 42 is completely deflated, so that the compression of the upper arm of the subject is removed.

Then, as illustrated in FIG. 14, the control unit 20 displays the blood pressure values as a measurement result on the display unit 21 and stores those blood pressure values in the memory unit 22 (step S211). Afterward, the control unit 20 ends the operation after receiving an instruction from the subject to turn off the power.

By employing a configuration as in this embodiment described above, it is possible to provide a flow rate control valve that can be configured to be compact, lightweight, and inexpensive, that achieves low power consumption, and that can easily control the flow rate of a fluid, and to provide a sphygmomanometer that can be configured to be compact, lightweight, and inexpensive, that achieves low power consumption, and that can easily control the flow rate of the compressed air that should be discharged from the compressing air bladder. Moreover, when a piezoelectric pump is used as the pressure generating unit as in this embodiment, it is also possible to provide a sphygmomanometer that achieves a reduced noise level during depressurizing operations.

Figure 17:
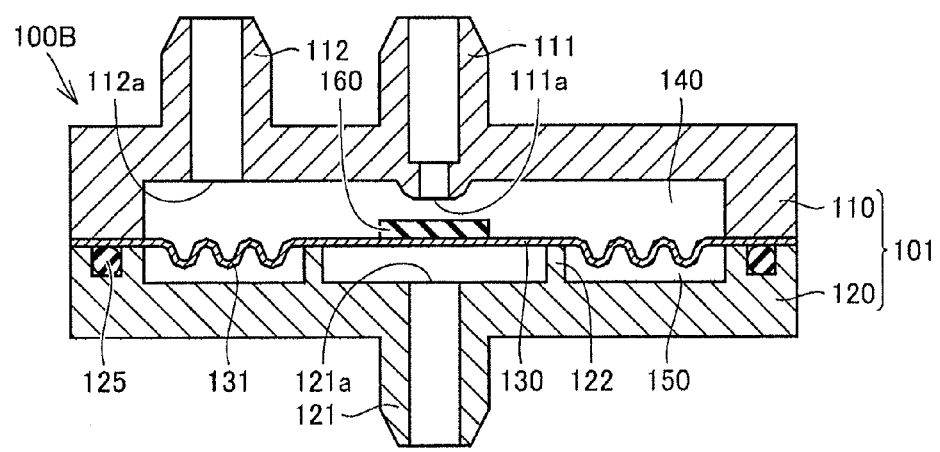
FIG. 17 is a schematic cross-sectional view of a valve unit of a flow rate control valve of a first variation according to Embodiment 1 of the invention.
Figure 18:
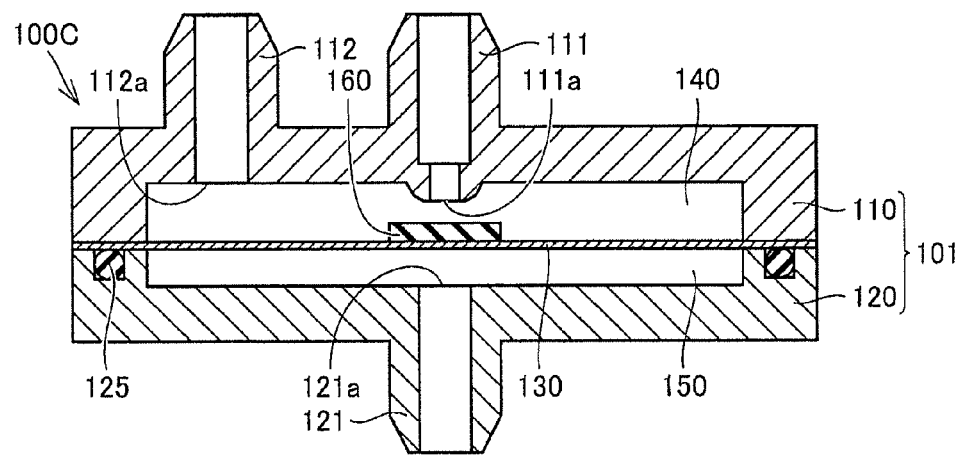
FIG. 18 is a schematic cross-sectional view of a valve unit of a flow rate control valve of a second variation according to Embodiment 1 of the invention.
Figure 19:
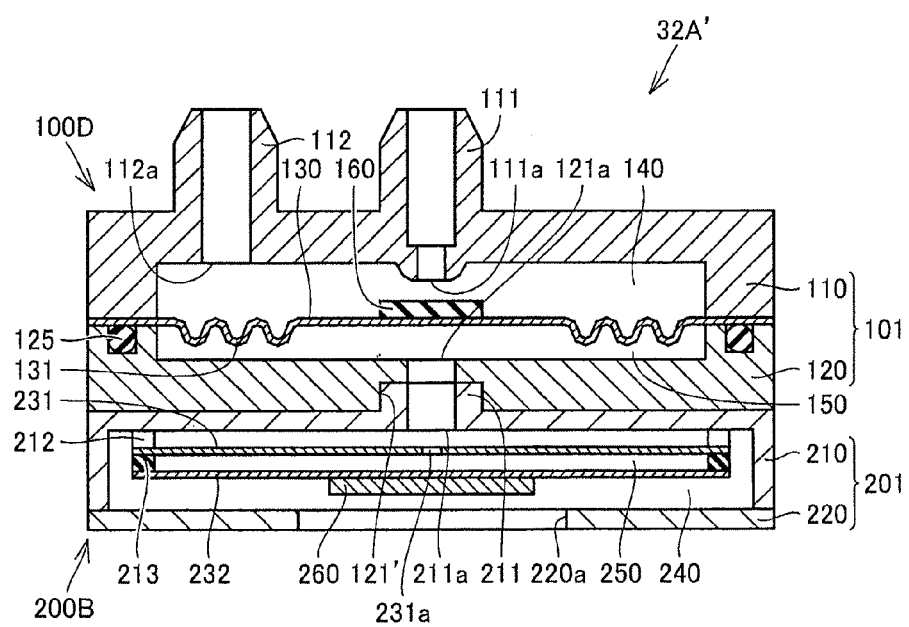
FIG. 19 is a schematic cross-sectional view of a flow rate control valve of a third variation according to Embodiment 1 of the invention.

FIGS. 17 and 18 are schematic cross-sectional views each showing a valve unit of a flow rate control valve of first and second variations, respectively, according to this embodiment, and FIG. 19 is a schematic cross-sectional view of a flow rate control valve of a third variation according to this embodiment. Next, with reference to FIGS. 17 to 19, the flow rate control valves of the first to third variations according to this embodiment will be described.

As shown in FIG. 17, a valve unit 100B of the flow rate control valve of the first variation is different from the valve unit 100A of the aforementioned flow rate control valve 32A of this embodiment in the configuration of the lower case 120. Specifically, the lower case 120 of the valve unit 100B is provided with a restricting portion 122 that restricts deflection of the diaphragm 130 toward the side of the working space 150. This restricting portion 122 is provided so as to protrude from a portion of the lower case 120 that faces the working space 150 toward the side of the upper case 110, and is configured so that in a state in which the diaphragm 130 is not deflected, the restricting portion 122 comes into contact with a principal surface of the diaphragm 130 on the side of the working space 150.

By providing a flow rate control valve including this valve unit 100B, it is possible to prevent the diaphragm 130 from being deflected more than necessary when, for example, quickly discharging the compressed air, the flow rate of which should be controlled, and it is possible to prevent breakage of the diaphragm 130. Therefore, in addition to the aforementioned effects, an effect of providing a flow rate control valve having still higher reliability can be achieved.

As shown in FIG. 18, a valve unit 100C of the flow rate control valve of the second variation is different from the valve unit 100A of the aforementioned flow rate control valve 32A of this embodiment in the configuration of the diaphragm 130. Specifically, the diaphragm 130 provided in the valve unit 100C has a flat plate-like shape and does not include the corrugated, easily deformable portion 131 as provided in the valve unit 100A of the aforementioned flow rate control valve 32A of this embodiment. When the diaphragm 130 having such a flat plate-like shape is employed, the same effects as the aforementioned effects can be achieved as well.

As shown in FIG. 19, a flow rate control valve 32A' of the third variation has a configuration in which a valve unit 100D and a piezoelectric pump unit 200B are integrated. Specifically, in the aforementioned flow rate control valve 32A of this embodiment, the valve unit 100A and the piezoelectric pump unit 200A are connected to each other via the connecting tube 52. However, in the flow rate control valve 32A' of this variation, a recessed connecting portion 121' is provided in the lower case 120 of the valve unit 100D, a protruding ejection portion 211 is provided in the upper side housing of the piezoelectric pump unit 200B, and the connecting portion 121' and the ejection portion 211 are fitted to each other, so that the need for the connecting tube 52 is eliminated, and the valve unit 100D and the piezoelectric pump unit 200B are integrated. It should be noted that in order to more firmly fix these units to each other, in addition to the above-described fitting, a fastening means such as a screw may also be used to fix these units.

By employing this configuration, in addition to the aforementioned effects, it is possible to achieve an effect of providing a flow rate control valve that can be configured to be even more compact and inexpensive. Moreover, since the volume of a communication path between the ejection port 211a of the piezoelectric pump unit 200A and the working space 150 can be minimized, an effect of enhancing the responsiveness of flow rate control can be achieved.

Embodiment 2

A sphygmomanometer of Embodiment 2 of the invention is the same as the sphygmomanometer 1 of Embodiment 1 of the invention described above except that the pressure generating unit provided in the flow rate control valve is different. In this embodiment, specifically, the flow rate control valve 32 is configured by a flow rate control valve 32B that is composed of the valve unit 100A, a motor pump unit 300, and an escape valve unit 400, which will be described later, and the flow rate control valve drive circuit 35 is configured by a motor drive circuit 35B that controls driving of a motor 360 provided in the motor pump unit 300 (see FIGS. 20 and 23 to 25, for example). Hereinafter, the flow rate control valve 32B of this embodiment will be described in detail.

Figure 20:
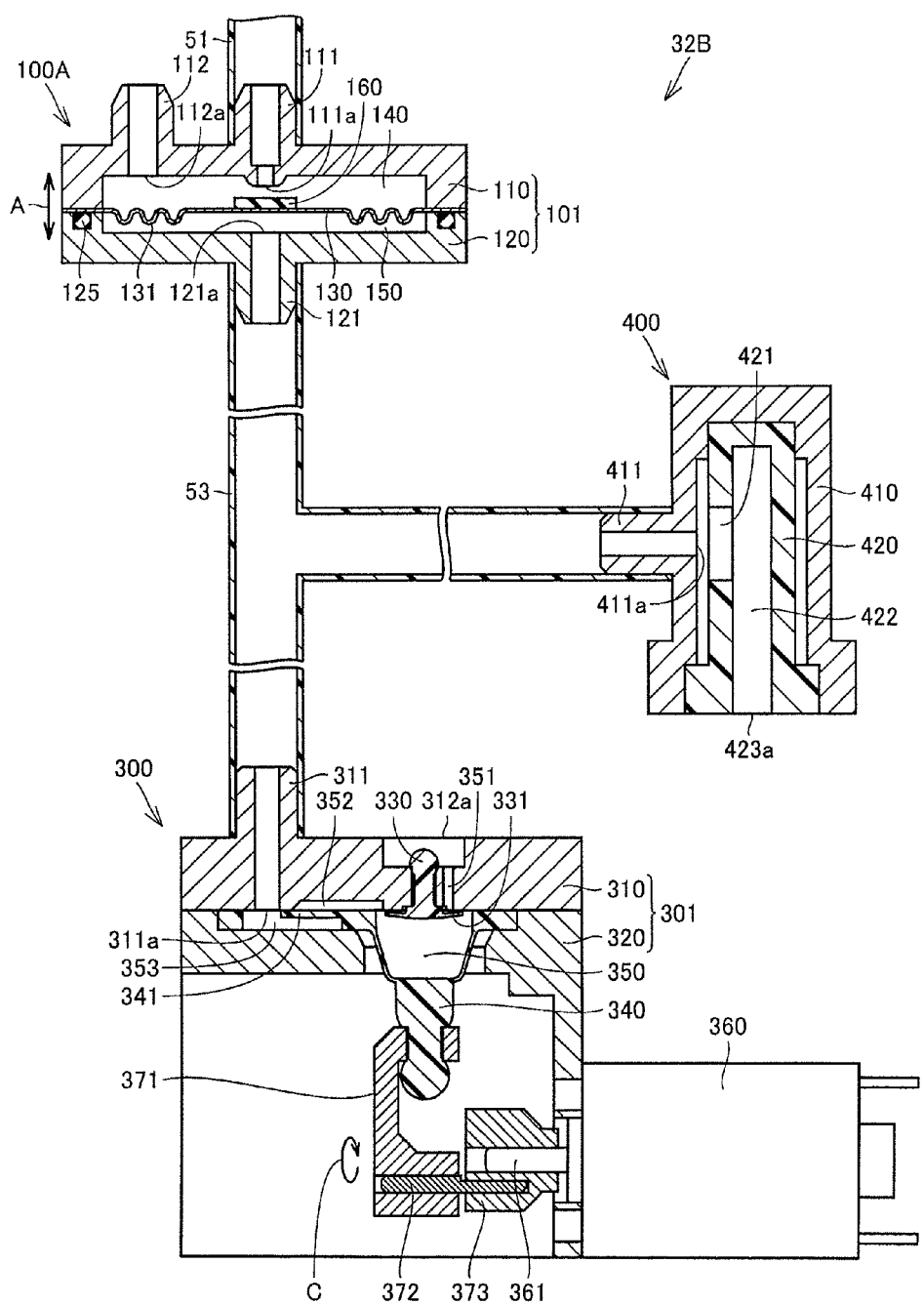
FIG. 20 is a schematic cross-sectional view of a flow rate control valve of Embodiment 2 of the invention.
Figure 21A:
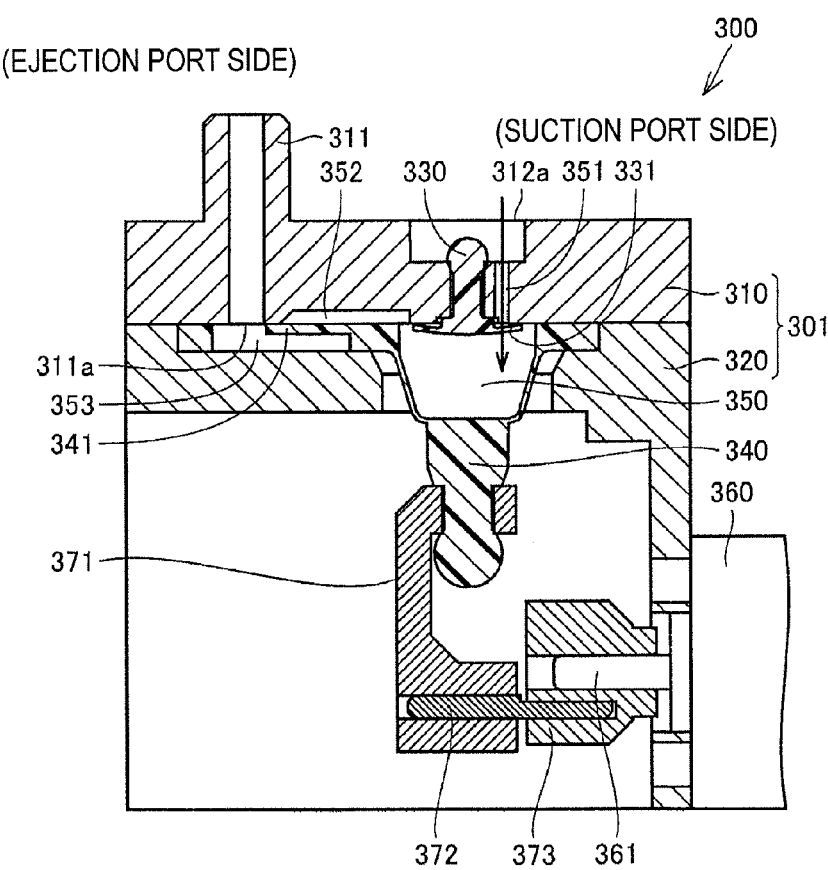
FIG. 21A is a schematic cross-sectional view showing an operating condition of a motor pump unit shown in FIG. 20.
Figure 21B:
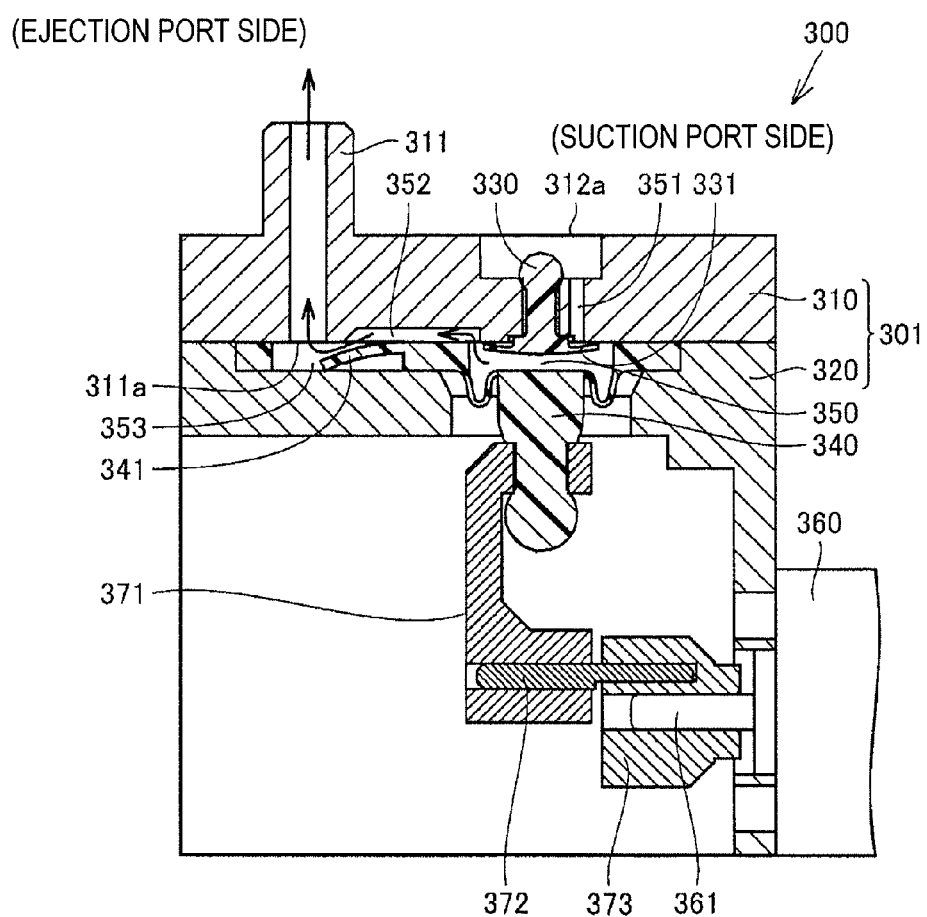
FIG. 21B is a schematic cross-sectional view showing an operating condition of the motor pump unit shown in FIG. 20.
Figure 22A:
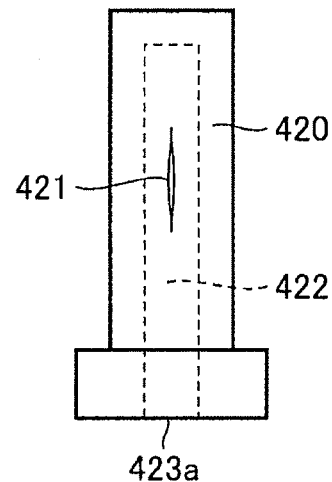
FIG. 22A is a side view showing the configuration of an escape valve unit shown in FIG. 20.
Figure 22B:
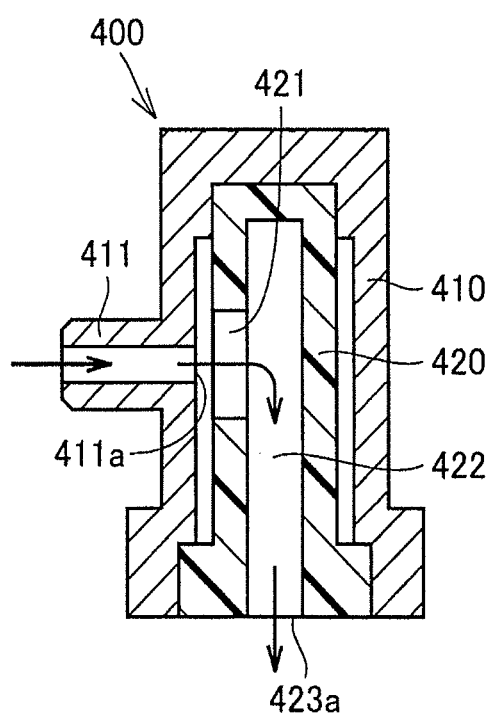
FIG. 22B is a schematic cross-sectional view showing an operating condition of the escape valve unit shown in FIG. 20.

FIG. 20 is a schematic cross-sectional view of the flow rate control valve of this embodiment. Moreover, FIGS. 21A and 21B are schematic cross-sectional views showing operating conditions of the motor pump unit of the flow rate control valve shown in FIG. 20, and FIGS. 22A and 22B are, respectively, a side view showing the configuration of the escape valve unit of the flow rate control valve shown in FIG. 20, and a schematic cross-sectional view showing an operating condition of the escape valve unit. Next, with reference to FIGS. 20 to 22B, a specific configuration of the flow rate control valve 32B of this embodiment, an operation of the motor pump unit 300, and an operation of the escape valve unit 400 will be described. It should be noted that in FIGS. 21A, 21B, and 22B, the flow of air serving as the working medium is schematically shown by arrows.

As shown in FIG. 20, the flow rate control valve 32B of this embodiment is configured by combining the valve unit 100A, the motor pump unit 300 serving as the pressure generating unit, and the escape valve unit 400. The valve unit 100A, the motor pump unit 300, and the escape valve unit 400 are connected to one another via a connecting tube 53. Moreover, the flow rate control valve 32B is connected to the compressing air bladder 42, the pressurization pump 31, and the pressure sensor 33 via the connecting tube 51.

The flow rate control valve 32B of this embodiment is configured so that the compressed air, the flow rate of which is to be controlled, can flow into the valve unit 100A from the compressing air bladder 42 via the connecting tube 51, air serving as the working medium can be introduced into the valve unit 100A from the motor pump unit 300 via the connecting tube 53, and air serving as the working medium can be released from the valve unit 100A into the escape valve unit 400 via the connecting tube 53. Therefore, in the flow rate control valve 32B, the pressure of air that is present in the valve unit 100A and serves as the working medium can be varied by controlling driving of the motor pump unit 300, and thus the flow rate of the compressed air flowing into the valve unit 100A is adjusted, so that the flow rate of the compressed air flowing out of the valve unit 100A can be variably controlled. It should be noted that the configuration of the valve unit 100A is the same as that of Embodiment 1 of the invention described above, and so descriptions thereof are not repeated here.

As shown in FIG. 20, the motor pump unit 300 mainly includes a housing 301, a first valve body 330, a second valve body 340, and a motor 360. The housing 301 is configured by combining a flat plate-shaped upper side housing 310, to which the first valve body 330 is attached and a lower side housing 320, to which the motor 360 is attached, and the second valve body 340 is held by the upper side housing 310 and the lower side housing 320 from both sides.

An ejection portion 311, to which the connecting tube 53 is connected, is provided at a predetermined position of the upper side housing 310, and an ejection port 311a through which air serving as the working medium is ejected is provided in the ejection portion 311. Moreover, a communication path 353 is provided in a portion of the lower side housing 320 that faces the ejection port 311a.

A communication path 351 is provided at a different predetermined position of the upper side housing 310 so as to pass through the upper side housing 310. A suction port 312a through which air serving as the working medium is suctioned is configured by an opening end of the communication path 351 that is located on the side of an upper surface of the upper side housing 310. Moreover, an opening end of the communication path 351 that is located on the side of a lower surface of the upper side housing 310 can be closed by a check valve portion 331 of the first valve body 330.

The second valve body 340 has a hollow portion inside, and is disposed such that the hollow portion faces the check valve portion 331 of the first valve body 330. A space that contains the above-described hollow portion and is defined mainly by the first valve body 330 and the second valve body 340 corresponds to a pumping space (pump compartment) 350. Moreover, a communication path 352 is provided in a portion of the upper side housing 310 that faces the pumping space 350.

A part of the communication path 352 provided in the upper side housing 310 and a part of the communication path 353 provided in the lower side housing 320 are arranged so as to face each other, and in that portion where the communication path 352 and the communication path 353 face each other, the communication path 352 can be closed by the check valve portion 341 of the second valve body 340.

A drive shaft 361 of the motor 360 that rotates in the direction of arrow C in the drawing is coupled to a lower end of the second valve body 340 via power transmission members 371 to 373. Thus, a rotational motion generated on the drive shaft 361 of the motor 360 is converted into a reciprocating motion in an approximately vertical direction by the power transmission members 371 to 373. As a result, the lower end of the second valve body 340 is driven by the motor 360 to move up and down, and thus the pumping space 350 pulsates.

Meanwhile, as shown in FIG. 20, the escape valve unit 400 includes a housing 410 that has a closed-bottomed tubular shape and a valve body 420 that has a closed-bottomed tubular shape and is inserted into the housing 410. A connecting portion 411 is provided at a predetermined position of the housing 410, and an opening 411a through which air serving as the working medium flows in is provided in that connecting portion 411.

As shown in FIG. 22A, a slit-shaped cut 421, which constitutes an escape port 421, is made in a portion of the valve body 420 that communicates with the opening 411a. The escape port 421 communicates with a discharge port 423a via the hollow portion 422 of the valve body 420.

FIGS. 21A and 21B both show a state in which the motor pump unit 300 is operated. In this operating state, a predetermined voltage is applied to the motor 360 to generate a rotational motion on the drive shaft 361 of the motor 360, which is then converted into a vertical motion of the lower end of the second valve body 340, so that the pumping space 350 pulsates.

At this time, as shown in FIG. 21A, in a state in which the pumping space 350 is expanded, a negative pressure is generated in the pumping space 350, and accordingly, the check valve portion 331 of the first valve body 330 is opened, and the check valve portion 341 of the second valve body 340 is closed. Thus, air serving as the working medium is suctioned through the suction port 312a into the pumping space 350 via the communication path 351.

After that, as shown in FIG. 21B, in a state in which the pumping space 350 is compressed, a positive pressure is generated in the pumping space 350, and accordingly, the check valve portion 331 of the first valve body 330 is closed, and the check valve portion 341 of the second valve body 340 is opened. Thus, air serving as the working medium is ejected through the ejection port 311a via the communication paths 352, 353.

When the above-described operations are repeated, the motor pump unit 300 exhibits a pump function of continuously ejecting air serving as the working medium through the ejection port 311a.

Here, unlike the aforementioned piezoelectric pump unit 200A, the motor pump unit 300 does not exhibit an escape function in a state in which driving thereof is stopped. That is to say, even under a condition that the pressure (usually at atmospheric pressure) on the side of the suction port 312a of the motor pump unit 300 is lower than the pressure on the side of the ejection port 311a (i.e., the internal pressure of the working space 150 of the valve unit 100A connected to the ejection portion 311), the check valve function of the aforementioned first valve body 330 and second valve body 340 prevents air serving as the working medium from flowing from the side of the ejection port 311a toward the side of the suction port 312a.

For this reason, in this embodiment, the aforementioned escape valve unit 400 is attached to the connecting tube 53 so as to communicate with the working space 150 of the valve unit 100A to enable the escape valve unit 400 to exhibit the escape function, and thus the internal pressure of the working space 150 of the valve unit 100A can be lowered.

As shown in FIG. 22B, under a condition that the pressure (usually at atmospheric pressure) on the side of the discharge port 423a of the escape valve unit 400 is sufficiently lower than the pressure on the side of the opening 411a (i.e., the internal pressure of the working space 150 of the valve unit 100A connected to the connecting portion 411), the flow of air as shown in the drawing will be generated. That is to say, air serving as the working medium will flow into the hollow portion 422 of the valve body 420 from the opening 411a via the escape port 421, and will be then discharged through the discharge port 423a. It should be noted that since the escape port 421 is formed by a cut, the escape port 421 has a considerable level of flow resistance, and the aforementioned flow of air is not generated unless the pressure on the side of the discharge port 423a becomes sufficiently lower than the pressure on the side of the opening 411a.

As described above, in the flow rate control valve 32B of this embodiment, the motor pump unit 300 exhibits the pump function of increasing the internal pressure of the working space 150 of the valve unit 100A, and the escape valve unit 400 exhibits the escape function of lowering and returning the internal pressure of the working space 150 of the valve unit 100A to atmospheric pressure.

Figure 23:
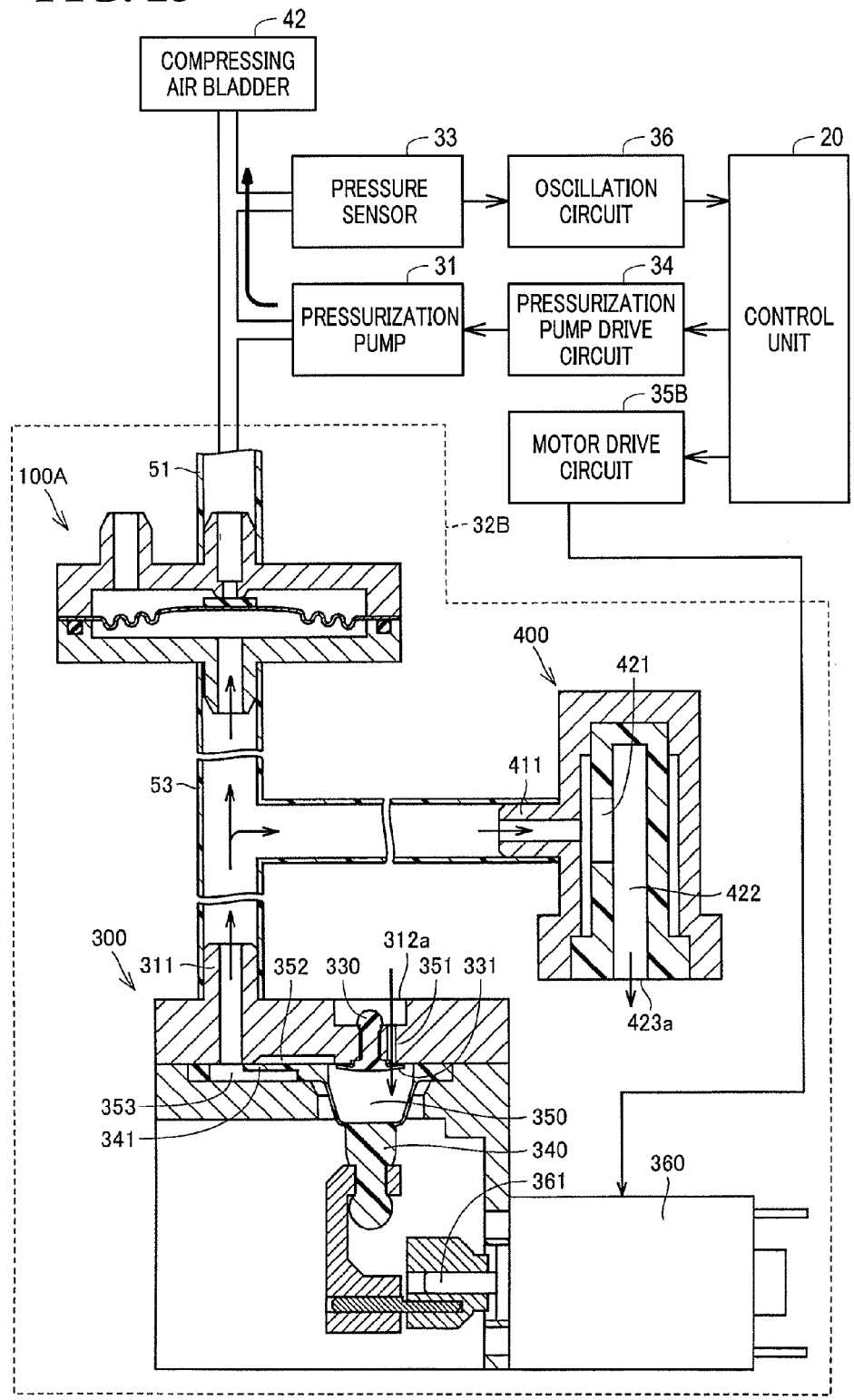
FIG. 23 is a diagram illustrating a specific operation of a sphygmomanometer of Embodiment 2 of the invention in a quick pressurization process according to the operation flow illustrated in FIG. 9.
Figure 24:
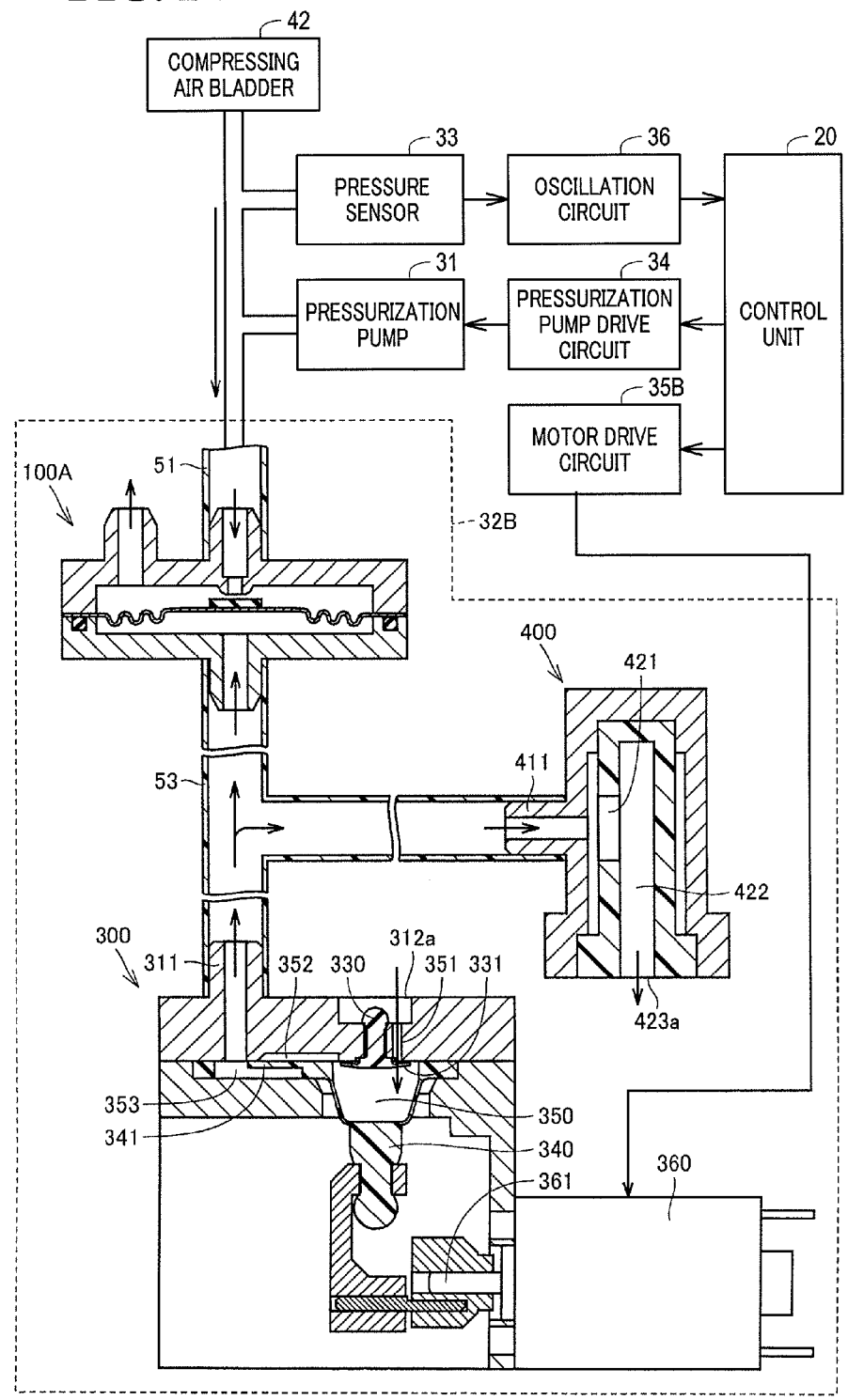
FIG. 24 is a diagram illustrating a specific operation of the sphygmomanometer of Embodiment 2 of the invention in a slow depressurization process according to the operation flow illustrated in FIG. 9.
Figure 25:
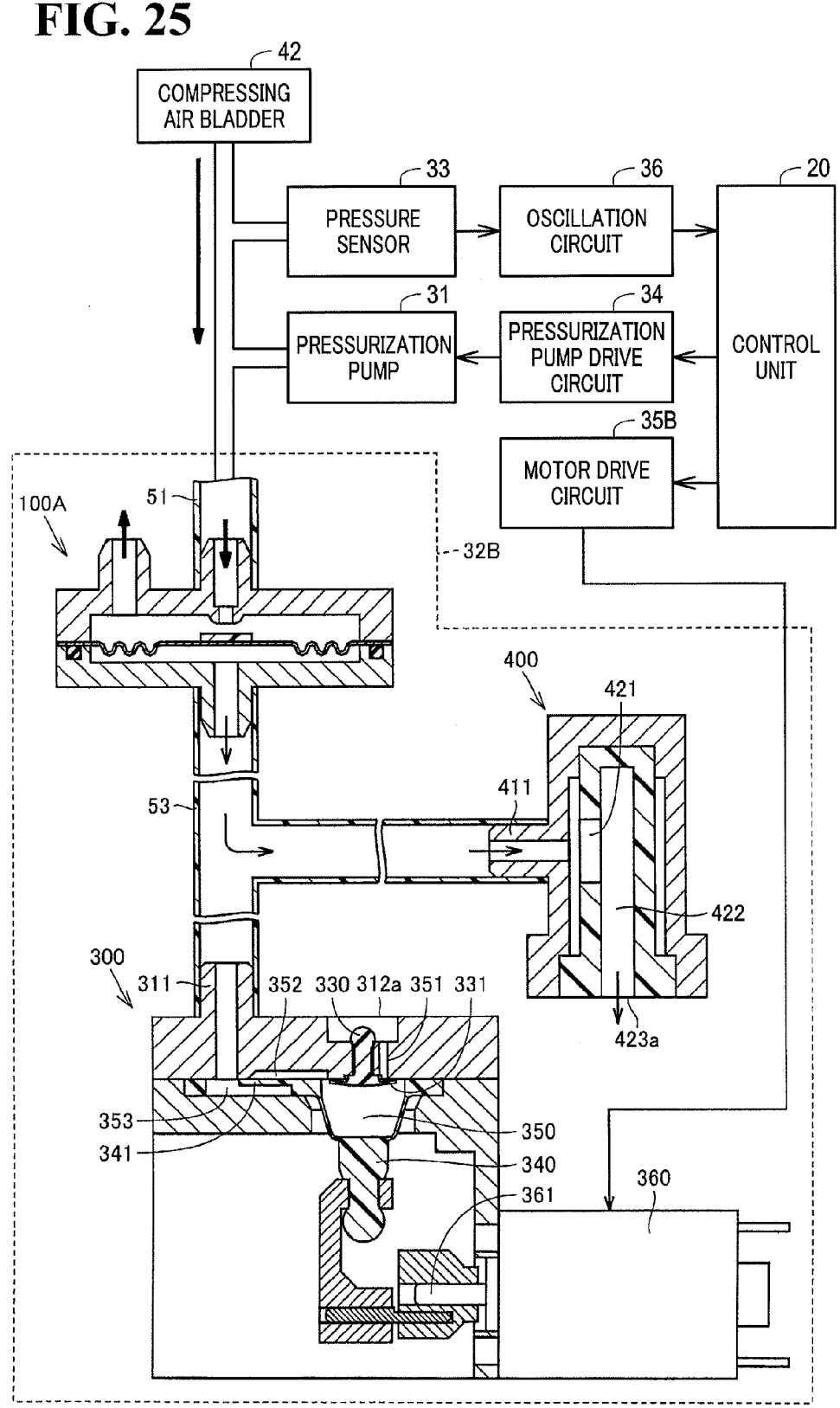
FIG. 25 is a diagram illustrating a specific operation of the sphygmomanometer of Embodiment 2 of the invention in a quick depressurization process according to the operation flow illustrated in FIG. 9.

FIGS. 23 to 25 are diagrams illustrating specific operations of the sphygmomanometer of this embodiment in a quick pressurization process, a slow depressurization process, and a quick depressurization process in the case where blood pressure measurement is performed using the sphygmomanometer according to an operation flow based on the depressurization measurement method. Next, with reference to FIGS. 23 to 25, a specific operation of the sphygmomanometer of this embodiment in the case where a blood pressure value is measured on the sphygmomanometer based on the depressurization measurement method will be described.

As shown in FIG. 23, in the sphygmomanometer of this embodiment, in the quick pressurization process, the control unit 20 gives a predetermined control signal to the pressurization pump drive circuit 34 to drive the pressurization pump 31 to feed the compressed air from the pressurization pump 31 into the compressing air bladder 42, and also gives a predetermined control signal to the motor drive circuit 35B to drive the motor pump unit 300 to introduce air serving as the working medium into the working space 150 of the valve unit 100A, thereby deflecting the diaphragm 130 to move the valve body 160 so that the inlet port 111a is fully closed by the valve body 160. The driving voltage applied to the motor 360 at this time is set to a magnitude of voltage that is sufficient to enable the valve body 160 to fully close the inlet port 111a. It should be noted that in determining this driving voltage, it is necessary to take into account that a part of air serving as the working medium will leak out via the escape valve unit 400.

As shown in FIG. 24, in the sphygmomanometer of this embodiment, in the slow depressurization process, the control unit 20 gives a predetermined control signal to the pressurization pump drive circuit 34 to stop the pressurization pump 31, and also gives a predetermined control signal to the motor drive circuit 35B to continue driving the motor pump unit 300 at a lowered output power to reduce the internal pressure of the working space 150, thereby reducing the deflection of the diaphragm 130 to move the valve body 160 so that the inlet port 111a is slightly opened. As a result, the compressed air that is present inside the compressing air bladder 42 is gradually discharged via the flow rate control valve 32A. The driving voltage applied to the motor 360 at this time is a voltage less than a magnitude of voltage that is sufficient to enable the valve body 160 to fully close the inlet port 111a, and that falls within a range that can restrict the flow rate of the compressed air entering through the inlet port 111a to a predetermined flow rate. It should be noted that in determining this driving voltage, it is necessary to take into account that a part of the air serving as the working medium will leak out via the escape valve unit 400.

As shown in FIG. 25, in the sphygmomanometer of this embodiment, in the quick depressurization process, the control unit 20 gives a predetermined control signal to the motor drive circuit 35B to stop the motor pump unit 300 to release air serving as the working medium from the working space 150 of the valve unit 100A, thereby reducing the deflection of the diaphragm 130 to move the valve body 160 so that the inlet port 111a is brought into a fully opened state. As a result, the compressed air that is present inside the compressing air bladder 42 is quickly discharged via the escape valve unit 400.

It should be noted that although not described here, in the sphygmomanometer of this embodiment, blood pressure values can be measured in accordance with an operation flow based on the pressurization measurement method as well, and the operation in that case is the same as in the case of the sphygmomanometer of Embodiment 1 of the invention described above.

When a configuration as in this embodiment described above is employed, as in the case where a configuration as in Embodiment 1 of the invention is employed, it is possible to provide a flow rate control valve that can be configured to be compact, lightweight, and inexpensive, that achieves low power consumption, and that can easily control the flow rate of a fluid, and to provide a sphygmomanometer that can be configured to be compact, lightweight, and inexpensive, that achieves low power consumption, and that can easily control the flow rate of the compressed air that should be discharged from the compressing air bladder.

Figure 26:
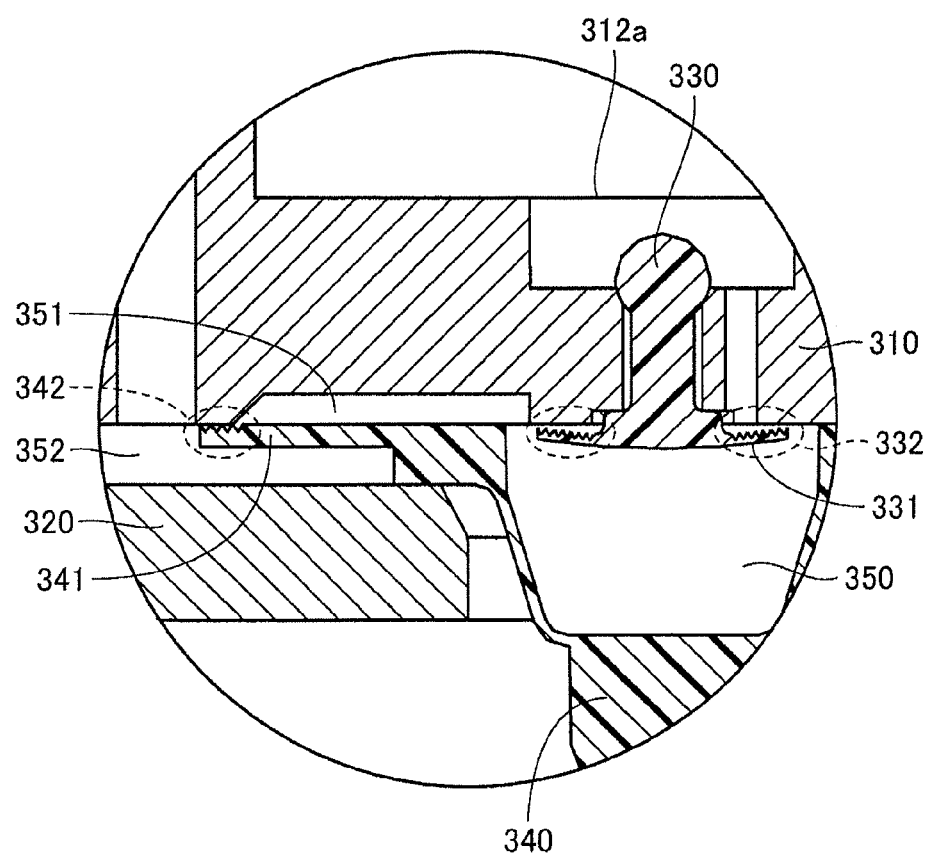
FIG. 26 is an enlarged cross-sectional view of a relevant portion of a motor pump unit of a flow rate control valve of a variation according to Embodiment 2 of the invention.

FIG. 26 is an enlarged cross-sectional view of a relevant portion of a motor pump unit of a flow rate control valve of a variation according to this embodiment. Next, with reference to FIG. 26, the motor pump unit of the flow rate control valve of the variation according to this embodiment will be described.

As shown in FIG. 26, the motor pump unit of the flow rate control valve of this variation is different from the motor pump unit of the above-described flow rate control valve 32B of this embodiment in the configurations of the first valve body 330 and the second valve body 340. Specifically, in the motor pump unit of the flow rate control valve of this variation, the check valve portion 331 of the first valve body 330 and the check valve portion 341 of the second valve body 340 are roughened by forming a large number of minute protrusions and recesses 332, 342 in these portions, and thus the sealability of the check valve portions 331, 341 is intentionally decreased. Therefore, the check valve portions 331, 341 exhibit the escape function of allowing air serving as the working medium to escape.

With this configuration, the need to separately provide the above-described escape valve unit 400 is eliminated. Therefore, in addition to the aforementioned effects, an effect of making it possible to configure a flow rate control valve that is even more compact, lightweight, and inexpensive and a sphygmomanometer including this flow rate control valve can be achieved.

In the embodiments of the invention and the variations thereof described above, the cases where a piezoelectric pump or a motor pump is used as the pressure generating unit were described as examples. However, it goes without saying that other pumps (including blowers) can also be used.

Moreover, in the foregoing descriptions of the embodiments of the invention and the variations thereof, a flow rate control valve that is configured so that the internal pressure of the working space is varied by introducing the working medium into the working space from the outside and releasing the working medium from the working space to the outside was used as an example. However, the flow rate control valve can also be configured so that the internal pressure of the working space is varied by, for example, sealing the working medium in the working space by hermetically closing the working space, and varying the volume of the sealed-in working medium.

Moreover, in the foregoing descriptions of the embodiments of the invention and the variations thereof, the cases where the fluid, the flow rate of which is controlled, is compressed air, and air is employed as the working medium were described as examples. However, the scope of application of the invention is not limited to these. The fluid, the flow rate of which is controlled, may also be a high-pressure gas other than compressed air, a liquid in a compressed environment, or the like, and the working medium may also be a gas other than air, a liquid, or the like.

Moreover, the characteristic configurations that were shown in the embodiments of the invention and the variations thereof described above can naturally be used in combination where necessary.

Furthermore, in the foregoing descriptions of the embodiments of the invention and the variations thereof, an upper arm sphygmomanometer for measuring blood pressure values such as a systolic blood pressure value and a diastolic blood pressure value was used as an example of the blood pressure information measurement device. However, it goes without saying that the invention can also be applied to a wrist sphygmomanometer, a leg sphygmomanometer, and a blood pressure information measurement device that enables measurement of the pulse wave or the pulse, an index indicating the level of arteriosclerosis, which is typified by the AI (Augmentation Index) value and the like, an average blood pressure value, oxygen saturation, and the like.

In this manner, the embodiments and variations thereof disclosed herein are to be considered in all respects as illustrative and not restrictive. The technical scope of the present invention is defined by the appended claims, and all changes that fall within the meaning and scope equivalent to those of the claims are intended to be embraced therein.

REFERENCE SIGNS LIST 1 sphygmomanometer
10 main body
20 control unit
21 display unit
22 memory unit
23 operation unit
24 power supply unit
30 compressing air system component
31 pressurization pump
32, 32A, 32A', 32B flow rate control valve
33 pressure sensor
34 pressurization pump drive circuit
35 flow rate control valve drive circuit
35A piezoelectric element drive circuit
35B motor drive circuit
36 oscillation circuit
40 cuff
41 outer package cover
42 compressing air bladder
50 air tube
51 to 53 connecting tube
100A to 100D valve unit
101 casing
110 upper case
111 inlet portion
111a inlet port
112 outlet portion
112a outlet port
120 lower case
121, 121' connecting portion
121a opening
122 restricting portion
125 seal member
130 diaphragm
131 easily deformable portion
140 flow space
150 working space
160 valve body
161 inclined surface
162 minute protrusions and recesses
200A, 200B piezoelectric pump unit
201 housing
210 upper side housing
211 ejection portion
211a ejection port
212 first support member
213 second support member
220 lower side housing
220a suction port
231 thin plate portion
231a minute communication hole
232 vibrating plate portion
240 pumping space
250 surrounding space
260 piezoelectric element
300 motor pump unit
301 housing
310 upper side housing
311 ejection portion
311a ejection port
312a suction port
320 lower side housing
330 first valve body
331 check valve portion
332 protrusions and recesses
340 second valve body
341 check valve portion
342 protrusions and recesses
350 pumping space
351 to 353 communication path
360 motor
361 drive shaft
371 to 373 power transmission member
400 escape valve unit
410 housing
411 connecting portion
411a opening
420 valve body
421 escape port
422 hollow portion
423a discharge port

The invention claimed is:

1. A flow rate control valve that can variably control a flow rate of a fluid to be supplied to a cuff for a blood pressure information measurement device, the flow rate control valve comprising:
a casing that is provided with an inlet port through which the fluid flows in from the cuff and an outlet port through which the fluid flows out, the inlet port being connected to the cuff and the outlet port being open to outside;
a single diaphragm that partitions a space within the casing into a flow space in which the fluid flows and a working space in which a working medium different from the fluid is present, the diaphragm separating the working medium from the fluid, and the inlet port and the outlet port each being connected to the flow space; and
a valve body that is provided on a portion of the diaphragm that opposes the inlet port,
wherein the diaphragm is displaced in accordance with a change in an internal pressure of the working space, the valve body is accordingly moved, resulting in a change in a distance between the valve body and the inlet port, and thus the flow rate of the fluid flowing into the flow space through the inlet port is adjusted, so that the flow rate of the fluid flowing out through the outlet port can be variably controlled.

2. The flow rate control valve according to claim 1, wherein a portion of the diaphragm that is displaced in accordance with a change in the internal pressure of the working space has a larger area than an opening area of the inlet port.

3. The flow rate control valve according to claim 1, wherein the valve body has a size that is sufficient to completely close the inlet port in a state in which the distance between the valve body and the inlet port is reduced to zero.

4. The flow rate control valve according to claim 1, wherein the valve body is made of an elastic member.

5. The flow rate control valve according to claim 1, wherein the valve body is made of a member that is harder than the diaphragm.

6. The flow rate control valve according to claim 1, wherein a principal surface of the valve body that opposes the inlet port has protrusions and recesses.

7. The flow rate control valve according to claim 1, wherein the casing is provided with an opening for introducing and releasing the working medium.

8. The flow rate control valve according to claim 7, further comprising a pressure generating unit configured to produce a change in the internal pressure of the working space by introducing and releasing the working medium via the opening.

9. The flow rate control valve according to claim 8, wherein the pressure generating unit includes a pump that suctions and ejects the working medium.

10. The flow rate control valve according to claim 9, wherein a direction from the side of a suction port to the side of an ejection port of the pump is a forward direction, the pump is composed of a pump that can discharge the working medium in a reverse direction to the forward direction under a condition that a pressure on the side of the suction port is lower than a pressure on the side of the ejection port.

11. The flow rate control valve according to claim 10, wherein the pump is a piezoelectric pump that suctions and ejects the working medium by vibration of a vibrating plate portion to which an piezoelectric element is attached.

12. The flow rate control valve according to claim 9, wherein
- a direction from the side of a suction port to the side of an ejection port of the pump is a forward direction, the pump is composed of a pump that cannot discharge the working medium in a reverse direction to the forward direction under a condition that a pressure on the side of the suction port is lower than a pressure on the side of the ejection port, and
- an escape valve is provided so as to communicate with the working space.

13. The flow rate control valve according to claim 9, wherein the casing and the pressure generating unit are integrated by fixing the casing to a housing of the pressure generating unit.

14. The flow rate control valve according to claim 1, wherein
- the fluid is compressed air that is compressed to a pressure greater than atmospheric pressure, and
- the working medium is air at a pressure lower than the compressed air.

15. A blood pressure information measurement device comprising the flow rate control valve according to claim 14 as a discharge valve for reducing an internal pressure of a compressing fluid bladder for compressing a living body.

16. The blood pressure information measurement device according to claim 15, wherein
- during measurement, driving of the flow rate control valve serving as the discharge valve is controlled so that the internal pressure of the compressing fluid bladder is reduced, and thus at least a systolic blood pressure value and a diastolic blood pressure value are calculated based on a depressurization measurement method, and
- after completion of measurement, driving of the flow rate control valve serving as the discharge valve is controlled so that the internal pressure of the compressing fluid bladder is reduced.

17. The blood pressure information measurement device according to claim 15, wherein
- during measurement, driving of the flow rate control valve serving as the discharge valve is controlled so that the internal pressure of the compressing fluid bladder is increased, and thus at least a systolic blood pressure value and a diastolic blood pressure value are calculated based on a pressurization measurement method, and
- after completion of measurement, driving of the flow rate control valve serving as the discharge valve is controlled so that the internal pressure of the compressing fluid bladder is reduced.

* * * * *